US008562995B2

(12) United States Patent
Müeller-Hermelink et al.

(10) Patent No.: US 8,562,995 B2
(45) Date of Patent: *Oct. 22, 2013

(54) NEOPLASM SPECIFIC ANTIBODIES AND USES THEREOF

(75) Inventors: Hans-Konrad Müeller-Hermelink, Wurzburg (DE); Heinz Peter Vollmers, Wurzburg (DE)

(73) Assignee: Patrys Limited, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/111,685

(22) Filed: May 19, 2011

(65) Prior Publication Data

US 2011/0287021 A1 Nov. 24, 2011

Related U.S. Application Data

(63) Continuation of application No. 10/549,052, filed as application No. PCT/IB2004/001186 on Mar. 15, 2004, now Pat. No. 7,947,812.

(30) Foreign Application Priority Data

Mar. 14, 2003 (DE) .................................. 103 11 248

(51) Int. Cl.
*C07K 16/18* (2006.01)
*A61K 39/00* (2006.01)
*A61P 35/00* (2006.01)

(52) U.S. Cl.
USPC ............... 424/155.1; 424/174.1; 424/130.1; 424/141.1; 514/19.3; 530/387.1; 530/388.1

(58) Field of Classification Search
None
See application file for complete search history.

(56) References Cited

U.S. PATENT DOCUMENTS

| | | | |
|---|---|---|---|
| 5,610,280 A | 3/1997 | Brandt et al. | |
| 5,639,863 A | 6/1997 | Dan | |
| 5,763,224 A | 6/1998 | Caras et al. | |
| 6,677,442 B1 | 1/2004 | Wang et al. | |
| 6,995,240 B1 | 2/2006 | Panayi et al. | |
| 7,049,132 B1 | 5/2006 | Lee | |
| 7,138,501 B2 * | 11/2006 | Ruben et al. | 530/388.23 |
| 2005/0123571 A1 | 6/2005 | Rossini et al. | |

FOREIGN PATENT DOCUMENTS

| | | |
|---|---|---|
| DE | 41 07 154 A1 | 4/1992 |
| DE | 692 12 671 T2 | 3/1997 |
| DE | 692 29 110 T2 | 11/1999 |
| DE | 695 27 975 T2 | 3/2003 |
| DE | 102 30 516 A1 | 1/2004 |
| EP | 0 502 812 A1 | 9/1992 |
| EP | 1 106 183 A2 | 6/2001 |
| EP | 1 106 183 A3 | 6/2001 |
| EP | 1 141 019 B1 | 4/2004 |
| WO | WO 96/16990 | 6/1990 |
| WO | WO 92/16624 | 10/1992 |
| WO | WO 97/02479 | 1/1997 |
| WO | WO 97/13844 A1 | 4/1997 |
| WO | WO 99/28461 | 6/1999 |
| WO | WO 99/53051 | 10/1999 |
| WO | WO 99/65935 A2 | 12/1999 |
| WO | WO 00/12562 | 3/2000 |
| WO | WO 00/37489 A2 | 6/2000 |
| WO | WO 00/37489 A3 | 6/2000 |
| WO | WO 01/62932 A1 | 8/2001 |
| WO | WO 01/83560 A1 | 11/2001 |
| WO | WO 02/02641 A1 | 1/2002 |
| WO | WO 02/12502 A2 | 2/2002 |
| WO | WO 02/84277 A1 | 10/2002 |
| WO | WO 03/011907 A3 | 2/2003 |
| WO | WO 03/076472 A2 | 9/2003 |
| WO | WO 03/076472 A3 | 9/2003 |
| WO | WO 2004/005351 A2 | 1/2004 |
| WO | WO 2004/020999 A1 | 3/2004 |
| WO | WO 2004/081027 A2 | 9/2004 |
| WO | WO 2004/081027 A3 | 9/2004 |
| WO | WO 2005/001052 A2 | 1/2005 |
| WO | WO 2005/045428 A2 | 5/2005 |
| WO | WO 2005/047332 A1 | 5/2005 |
| WO | WO 2005/065418 A2 | 7/2005 |
| WO | WO 2005/085862 A1 | 9/2005 |
| WO | WO 2005/092922 A2 | 10/2005 |
| WO | WO 2005/092922 A3 | 10/2005 |
| WO | WO 2005/094159 A2 | 10/2005 |

OTHER PUBLICATIONS

Skolnick and Fetrow. From genes to protein structure and function: novel applications of computational approaches in the genomic era. Trends in Biotechnology, 2000. vol. 18, pp. 34-39.*

Mac Callum, Martin, and Thornton. Antibody-antigen interactions: contact analysis and binding site topography. Journal of Molecular Biology, 1996. vol. 262, pp. 732-745.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*

Wu, Nie, Huse, and Watkins. Humanization of a murine monoclonal antibody by simultaneous optimization of framework and CDR residues. Journal of Molecular Biology, 1999. vol. 294, pp. 151-162.*

Rudikoff, Giusti, Cook, and Scharff. Single amino acid substitution altering antigen-binding specificity. Proceedings of the National Academy of Sciences, 1982. vol. 79 p. 1979.*

(Continued)

*Primary Examiner* — Hong Sang
*Assistant Examiner* — Michael D Allen
(74) *Attorney, Agent, or Firm* — Pillsbury Winthrop Shaw Pittman LLP

(57) ABSTRACT

The present invention features polypeptides, such as antibodies, and their use in the treatment and diagnosis of neoplasms.

7 Claims, 7 Drawing Sheets

(56) References Cited

OTHER PUBLICATIONS

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

DSMZ On-line Catalog, 2004. Listings for Colo-699, DV-90, EPLC-272H, and LOU-NH91.*

Albert, Alexandra L. et al., Multisite phosphorylation of Pin 1-associated mitotic phosphoproteins revealed by monoclonal antibodies MPM-2 and CC-3, BMC Cell Biology 2004, 5:22, published Jun. 1, 2004, pp. 1-13.

Barboro, Paola, et al., Differential Proteomic Analysis of Nuclear Matrix in Muscle-Invasive Bladder Cancer: Potential to Improve Diagnosis and Prognosis, Cellular Oncology 30 (2009) 13-26.

Basu, Amitabha et al. The Intracisternal A-Particle Proximal Enhancer-Binding Protein Activates Transcription and Is Identical to the RNA- and DNA-Binding Protein p54$^{nrb}$/NonO, Molecular and Cellular Biology, Feb. 1997, vol. 17, No. 2, p. 677-686.

Berger, C.L., et al., A Lymphocyte Cell Surface Heat Shock Protein Homologous to the Endoplasmic Reticulum Chaperone, Immunoglobulin Heavy Chain Binding Protein BIP, Int. J. Cancer, 71:1077-1085 (1997).

Bjorge et al., Complement-Regulatory Proteins in Ovarian Malignancies, Int. J. Cancer, 70:14-25 (1997).

Brandlein et al., "Natural IgM Antibodies and Immunosurveillance Mechanisms Against Epithelial Cancer Cells in Humans," Cancer Research, 63: 7995-8005, Nov. 15, 2003.

Brändlein et al., Characterization of Five New Fully Human Monoclonal IgM Antibodies Isolated from Carcinoma Patients, Proceedings of the Annual Meeting of the American Association for Cancer Research 43:970, Mar. 2002 (Abstract).

Brändlein et al., Human Monoclonal IgM Antibodies with Apoptotic Activity isolated from Cancer Patients, Human Antibodies 11:107-119, 2002.

Brändlein, S., et al., CFR-1 Receptor as Target for Tumor-specific Apoptosis Induced by the Natural Human Monoclonal Antibody PAM-1, Oncology Reports, 11:777-784 (2004).

Brändlein, S., et al., Cysteine-rich Fibroblast Growth Factor Receptor 1, a New Marker for Precancerous Epithelial Lesions Defined by the Human Monoclonal Antibody PAM-1, Cancer Research, 63:2052-2061 (2003).

Brändlein, S., et al., PAM-1, a Natural Human IgM Antibody as New Tool for Detection of Breast and Prostate Precursors, Human Antibodies, 13:97-104 (2004).

Brown, Carolyn J., et al., Expression of Genes from the Human Active and Inactive X Chromosomes, Am. J. Hum. Genet. 60:1333-1343, 1997.

Brown, Steven A., PERIOD1-Associated Proteins Modulate the Negative Limb of the Mammalian Circadian Oscillator, www.sciencemag.org, Science, vol. 308, Apr. 29, 2005, pp. 693-696.

Chen, G., et al., Protein Profiles Associated With Survival in Lung Adenocarcinoma, www.pnas.org/cgi/doi/10.1073/pnas.2233850100 pp. 1-6 (2003).

Clark, Jeremy, et al., Fusion of Splicing Factor Genes PSF and NonO (p54$^{nrb}$) to the TFE3 Gene in Papillary Renal Cell Carcinoma, Oncogene 15 (1997) 2233-2239.

Database entry AAB02178 dated Jun. 11, 1996.

Dong, Benhao et al, Purification and cDNA cloning of HeLa cell p54$^{nrb}$, a nuclear protein with two RNA recognition motifs and extensive homology to human splicing factor PSF and Drosophila NONA/BJ6, 1993 Oxford University Press, Nucleic Acids Research, 1993, Vol.

Emili, Andrew, et al., Splicing and Transcription-Associated Porteins PSF and p54$^{nrb}$/NonO Bind to the RNA Polymerase II CTD, RNA, 8 (2002) 1102-1111.

Exhibit to Data Sheet FR: correspondence with Imgenex on Feb. 11, 2009, pp. 1-2.

Exhibit to Data Sheet PR: correspondence with Everest Biotech on Feb. 11, 2009 (one page).

Exhibit to Data Sheets HR—KR: correspondence with LifeSpan Biosciences on Feb. 12, 2009, pp. 1-2.

Exhibit to Data Sheets RR—VR: correspondence with Novus Biologicals Inc. between Feb. 12-13, 2009 (2 pages).

Exhibit to Data Sheets YR—DDR: correspondence with Santa Cruz Biotechnology, Inc. on Feb. 12, 2009, pp. 1-3.

Faller et al., HAB-1, a New Heteromyeloma for Continuous Production of Human Monoclonal Antibodies, Br. J. Cancer 62:595-598 (1990).

Fox, Archa H. et al., Paraspeckles: A Novel Nuclear Domain, Current Biology, vol. 12, 13-25, Jan. 8, 2002, pp. 13-25.

Grossman, H.B., Natural Antibody to a Human Bladder Carcinoma Cell Line, Cancer Immunol. Immunother. 13:89-92 (1982).

Hensel et al., A New Variant of Cystein-Rich FGF Receptor (CFR-1) Specifically Expressed on Tumor Cells, Proceedings of the American Association for Cancer Research 41:698 (abstract 4438), Mar. 2000.

Hensel et al., A Novel Proliferation-associated Variant of CFR-1 Defined by a Human Monoclonal Antibody, Laboratory Investigation 81:1097-1108, 2001.

Hensel et al., Characterization of Glycosylphosphatidylinositol-linked Molecule CD55/Decay-accelerating Factor as the Receptor for Antibody SC-1-induced Apoptosis, Cancer Research 59:5299-5306, 1999.

Hensel et al., Mitogenic Autoantibodies in Helicobacter pylori-Associated Stomach Cancerogenesis, International Journal of Cancer 81:229-235, 1999.

Hensel, F., et al., "Regulation of the new coexpressed CD55 (decay-accelerating factor) receptor on stomach carcinoma cells involved in antibody SC-1-induced apoptosis", Laboratory Investigation, 81(11):1553-1563 (2001).

Huang et al., Sulindac Sulfide-induced Apoptosis Involves Death Receptor 5 and the Caspase 8-dependent Pathway in Human Colon and Prostate Cancer Cells, Cancer Research 61:6918-6924 (2001).

Ishiguro, Hitoshi, et al., 55 kDa Nuclear Matrix Portein (nmt55) mRNA is Expressed in Human Prostate Cancer Tissue and is Associated with the Androgen Receptor, Int. J. Cancer, 105 (2003) 26-32.

Iwadate, Y., et al., Molecular Classification and Survival Prediction in Human Gliomas Based on Proteome Analysis, Cancer Research, 64:2496-2501 (2004).

Jamora, C., et al., Inhibition of Tumor Progression by Suppression of Stress Protein GRP78/BiP Induction in Fibrosarcoma B/C10ME, Proc. Natl. Acad. Sci. USA, 93:7690-7694 (1996).

Jansson, et al., The Human Repertoire of Antibody Specificities Against Thomsen-Friedenreich and TN-carcinoma-associated antigens as defined by Monoclonal Antibodies, Cancer Immunology 34:294-298, 1992.

Kamitani, H., et al., Expression of 15-Lipoxygenase by Human Colerectal Carcinoma Caco-2 Cells During Apoptosis and Cell Differentiation, The Journal of Biological Chemistry, 273(34):21569-21577 (1998).

Kaneko, Syuzo, et al., The Multifunctional Portein p54nrb/PSF Recruits the Exonuclease XRN2 to Facilitate pre-mRNA 3' Processing and Transcription Termination, Genes & Dev., 21 (2007) 1779-1789.

Liang Songchun, et al., p54$^{nrb}$ is a Component of the snRNP-Free U1A (SF-A) Complex that Promotes pre-mRNA Cleavage During Polyadenylation, RNA, 12 (2006) 111-121.

Liang, Songchun et al., p54$^{nrb}$ is a component of the snRNP-free U1A (SF-A) complex that promotes pre-mRNA cleavage during polyadenylation, RNA (2006) 12:111-121.

Liu et al., Towards Proteome-Wide Production of Monoclonal Antibody by Phage Display, J. Mol. Bio. 315:1063-1073 (2002).

(56) References Cited

OTHER PUBLICATIONS

Mammalian Gene Collection (MGC) Program Team, "Generation and Initial Analysis of more than 15,000 Full-Length Human and Mouse cDNA Sequences" PNAS USA 99:16,899-16,903 (2002).

Masatoshi, K., Antibody CDNA, Abstract JP Publication No. 09098786 0, Apr. 15, 1997.

Mintz, P.J., et al., Fingerprinting the Circulating Repertoire of Antibodies from Cancer Patients, Nature Biotechnology, 21:57-63 (2003).

Mourelatos et al., Cloning and Sequence Analysis of the Human MG160, a Fibroblast Growth Factor and E-Selectin Binding Membrane Sialoglycoprotein of the Golgi Apparatus, DNA Cell Biol. 12:1121-1128 (1996).

Pavao, Matthew et al., Immunodetection of nmt55/p54$^{nrb}$ isofornns in human breast cancer, BMC Cancer 2001, 1:15, Published Oct. 29, 2001, (10 pages) http://www.biomedcentral.com/1471-2407/1/15.

Pavao, Matthew, et al., Immunodetection of nmt55/p54$^{nrb}$ Isoforms in Human Breast Cancer, BMC Cancer, 1:15 (2001).

Pfaff, M., et al., Human Monoclonal Antibody Against a Tissue Polypeptide Antigen-related Protein from a Patient with a Signet-Ring Cell Carcinoma of the Stomach, Cancer Research, 50:5192-5198 (1990).

Pohle et al., Lipoptosis: Tumor Specific Cell Death by Antibody-Induced Intracellular Lipid Accumulation, Cancer Research, 64:11, 3900-3906 (2004).

Proteau, Ariane, et al., The Multifunctional Nuclear Protein p54$^{nrb}$ is Multiphosphorylated in mitosis and Interacts with the Mitotic Regulator Pin1, J. Mol. Biol. 346 (2005) 1163-1172.

Sato, K., et al., Immunotherapy Using Heat-Shock Protein Preparations of Leukemia Cells After Syngenic Bone Marrow Transplantation in Mice, Blood, 98(6):1852-1857 (2001).

Shav-Tal, Yaron et al., PSF and p54$^{nrb}$/NonO—multi-functional nuclear proteins, Minireview, FEBS Letters 531 (2002), pp. 109-114.

Shav-Tal, Yaron, et al., Minireview PSF and p54$^{nrb}$/NonO-Multi-Functional Nuclear Proteins, FEBS Letters, 531 (2002) 109-114.

Stier, Sebastian, et al., Identification of p54$^{nrb}$ and the 14-2-2 Protein HS1 and TNF-α-Inducible Genes Related to Cell Cycle Control and Apoptosis in Human Arterial Endothelial Cells, Journal of Biochemistry and Molecular Biology, 38(4) (2005) 447-456.

Sugawara, S., et al., Suppression of Stress Protein GRP78 Induction in Tumor B/C10ME Eliminates Resistance to Cell Mediated Cytotoxicity, Cancer Research, 53:6001-6005 (1993).

Timmermann W., et al.,"Immunotherapy: an Antibody Against Stomach Cancer" Blick Jan. 1999, Artikel 6, internet page http://www.uni-wuerzburg.de/blick1999-1/991do6-t.html.

Traish, Abdulmaged M., et al., Loss of Expression of a 55 kDa Nuclear Protein (nmt55) in Estrogen Receptor-Negative Human Breast Cancer, Diagnostic Molecular Pathology, 6(4) (1997) 209-221.

Vollmers et al., "Apoptosis of Stomach Carcinoma Cells Induced by a Human Monoclonal Antibody," Cancer 76:550-558 (1995).

Vollmers et al., "Human Monoclonal Antibodies from Stomach Carcinoma Patients React with *Helicobacter pylori* and Stimulate Stomach Cells in vitro," Cancer 74:1525-1532, 1994.

Vollmers et al., "SC-1, a Functional Human Monoclonal Antibody against Autologous Stomach Carcinoma Cells," Cancer Res. 49:2471-2476, 1989.

Vollmers et al., Adjuvant Therapy for Gastric Adenocarcinoma with the Apoptosis-Inducing Human Monoclonal Antibody SC-1: First Clinical and Histopathological Results, Oncology Reports 5:549-552 (1998).

Vollmers, H.P., et al., Monoclonal Antibodies NORM-1 and NORM-2 Induce More Normal Behavior of Tumor Cells in Vitro and Reduce Tumor Growth In Vivo, Cell, 40:547-557 (1985).

Vollmers, P., et al., Tumor-Specific Apoptosis Induced by the Human Monoclonal Antibody SC-1: A New Therapeutical Approach for Stomach Cancer, Oncology Reports, 5:35-40 (1998).

Wixler et al., "Identification of Novel Interaction Partners for the conserved membrane proximal region of alpha-integrin cytoplasmic domains," FEBS Letters vol. 445, Feb. 26, 1999.

Zhang, Zuo, et al., The Fate of dsRNA in the Nucleus: A p54$^{nrb}$-Containing Complex Mediates the Nuclear Retention of Promiscuously A-to-I Edited RNAs, Cell, vol. 106, Aug. 24, 2001, pp. 465-475.

\* cited by examiner

```
                                                                                        CDR1
ccg acc ctg tcc ctc acc tgc gct gtc tct ggt ggc tcc atc agc agt ggt ggt tac tac                60
Pro Thr Leu Ser Leu Thr Cys Ala Val Ser Gly Gly Ser Ile Ser Ser Gly Gly Tyr Tyr
  1                   5                      10                      15                     20 tgg agc tgg atc cgc cag cac cca ggg aag ggc ctg gag tgg att ggg tac atc tat tac               120
Trp Ser Trp Ile Arg Gln His Pro Gly Lys Gly Leu Glu Trp Ile Gly Tyr Ile Tyr Tyr
                        25                      30                      35                  40
         CDR2
agt ggg agc acc tac tac aac ccg tcc ctc aag agt cga gtt acc ata tca gta gac acg               180
Ser Gly Ser Thr Tyr Tyr Asn Pro Ser Leu Lys Ser Arg Val Thr Ile Ser Val Asp Thr
                        45                      50                      55                  60 tct aag aac cag ttc tcc ctg aag ctg agc tct gtg act gcc gcg gac acg gcc gtg tat               240
Ser Lys Asn Gln Phe Ser Leu Lys Leu Ser Ser Val Thr Ala Ala Asp thr Ala Val Tyr
                        65                      70                      75                  80
                                             CDR3         D-region
tac tgt gcg aga gtt gat gcg cga tat gat tac gtt tgg agt tat cgt tat gat gct                   300
Tyr Cys Ala Arg Val Asp Ala Arg Tyr Asp Tyr Val Trp Gly Ser Tyr Arg Tyr Asp Ala
                        85                      90                      95                 100
        J-region
ttt gat atc tgg ggc caa gga acc atg gtc acc                                                   330
Phe Asp Ile Trp Gly Gln Gly Thr Met Val Thr
                       105                     110
```

FIG. 7

NEOPLASM SPECIFIC ANTIBODIES AND USES THEREOF

CROSS-REFERENCE TO RELATED APPLICATIONS

This application is a continuation application of U.S. Ser. No. 10/549,052, filed Sep. 13, 2005, which is a National Phase application of International Application No. PCT/IB2004/001186, filed Mar. 15, 2004 which designated the U.S. and that International Application was published under PCT Article 21(2) in English, and claims priority to German Application No. DE 103 11 248.0, filed Mar. 14, 2003, all of which applications are incorporated herein by reference in their entirety.

BACKGROUND OF THE INVENTION

The present invention is related to the field of cancer diagnosis and treatment and, more specifically, to the identification of polypeptides, such as antibodies, useful in the diagnosis, detection, monitoring, and treatment of neoplasms in a mammal, e.g., a human.

In the United States well over one million individuals are diagnosed with cancer each year. Although recent advances in the medical field have significantly improved the rate of survival among cancer patients, a large number of cancer-related deaths still could be prevented by the early diagnosis of the tumor. Accordingly, at the time of initial diagnosis, an alarming number of patients have already reached late stages of the disease.

With respect to colorectal cancer, the prognosis is usually poor in 50% of all cases because the tumor is often undetected until the disease has spread and reached a terminal stage. Similarly, approximately 75% of women are diagnosed with ovarian cancer after the disease has already reached an advanced stage (stage III or IV) because the symptoms of ovarian cancer are often vague or "silent." Despite aggressive surgical intervention and new chemotherapeutic regimens, the overall 5-year survival rate for these women with advanced stage ovarian cancer has remained constant over the past 30 years, at approximately 15%. Conversely, women diagnosed with cancer confined to the ovary (stage I) have an overall 5-year survival rate approaching 90%.

Clearly, there is a need for the early and improved detection and treatment of neoplasms (e.g., stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, or adenocarcinoma of the uterus), as this would increase the chance of treating the neoplasm and, thereby, lead to an improved prognosis for long-term survival.

SUMMARY OF THE INVENTION

We have discovered a class of polypeptides that react with an epitope specific for neoplastic cells. These polypeptides are not only excellent diagnostic tools, but also can induce apoptosis of the neoplastic cells to which they bind. This latter characteristic results in a treatment for neoplastic diseases that lacks the side-effects of many existing therapeutics.

The present invention features polypeptides, such as monoclonal antibodies that may be used in the diagnosis and treatment of a neoplasm, as well as the antigen recognized by such polypeptides. Accordingly, the first aspect of the invention features a purified polypeptide that specifically binds to a neoplastic cell, but does not bind to a non-neoplastic cell. This purified polypeptide specifically binds to a diffuse-type stomach adenocarcinoma, an intestinal-type stomach adenocarcinoma, an adenocarcinoma of the colon, an adenocarcinoma of the lung, a squamous cell carcinoma of the lung, a squamous cell carcinoma of the esophagus, an adenocarcinoma of the pancreas, a urothel carcinoma of the urinary bladder, a renal cell carcinoma of the kidney, an adenocarcinoma of the prostate, an invasive ductal carcinoma of the breast, an invasive lobular carcinoma of the breast, an adenocarcinoma of the ovary, and an adenocarcinoma of the uterus, and not to non-neoplastic cells of the same tissue type, and the purified polypeptide is substantially identical to the full-length sequence of SEQ ID NO:2.

In desirable embodiments of the first aspect of the invention, the polypeptide specifically binds to at least one of the following: lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393). Desirably, the polypeptide can induce apoptosis of the neoplastic cell, but not of the non-neoplastic cell or the polypeptide can decrease proliferation of the neoplastic cell, but not of the non-neoplastic cell.

The second aspect of the invention features a purified polypeptide containing the amino acid sequence of SEQ ID NO:2 and the third aspect of the invention features a purified polypeptide containing amino acids 16-22, 37-52, and 85-103 of SEQ ID NO:2.

In desirable embodiments of the second and third aspects of the invention, the purified polypeptide specifically binds to a diffuse-type stomach adenocarcinoma, an intestinal-type stomach adenocarcinoma, an adenocarcinoma of the colon, an adenocarcinoma of the lung, a squamous cell carcinoma of the lung, a squamous cell carcinoma of the esophagus, an adenocarcinoma of the pancreas, a urothel carcinoma of the urinary bladder, a renal cell carcinoma of the kidney, an adenocarcinoma of the prostate, an invasive ductal carcinoma of the breast, an invasive lobular carcinoma of the breast, an adenocarcinoma of the ovary, and/or an adenocarcinoma of the uterus, and not to non-neoplastic cells of the same tissue type.

In other desirable embodiments of the first three aspects of the invention, the polypeptide is an antibody or a functional fragment thereof, for example, a monoclonal antibody or a functional fragment thereof. Examples of functional fragments include $V_L$, $V_H$, $F_v$, $F_c$, Fab, Fab', and $F(ab')_2$ fragments. Further, the purified polypeptide of the first three aspects of the invention desirably is also produced by the LM-1 cell line having DSMZ Deposit Accession No. DSM ACC2623.

The fourth aspect of the invention features a functional fragment of an antibody that includes amino acids 16-22, 37-52, and/or 85-103 of SEQ ID NO:2. Desirably, this functional fragment is a functional fragment of a monoclonal antibody or a $V_H$ chain of an antibody.

In the fifth aspect, the invention features a purified polypeptide that is specifically bound by an antibody, or functional fragment thereof, containing the sequence of SEQ ID NO:2. Desirably, the polypeptide of the fifth aspect of the invention is a polypeptide expressed by lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383) or lung squamous cell carcinoma cell line LOU-NH91 (DSMZ accession number ACC 393), but not by non-neoplastic cells of the same tissue type. In another desirable embodiment of the fifth aspect, the polypeptide has an apparent molecular weight of approximately 70 kDa using sodium dodecyl sulfate polyacrylamide gel electrophoresis. In further desirable embodiments, the polypeptide of the fifth aspect, if present on a cell and bound by the antibody or functional fragment thereof, results in apoptosis of the cell or results in a reduction in proliferation of the cell.

In the sixth aspect, the invention features an isolated nucleic acid molecule containing the sequence of SEQ ID NO:1 and in the seventh aspect, the invention features an isolated nucleic acid molecule including nucleic acids 46-66, 109-156, and/or 253-309 of SEQ ID NO:1.

The eighth aspect of the invention features a vector including the nucleic acid sequence of the sixth or seventh aspects of the invention. In the ninth aspect, the invention features an isolated cell containing the vector of the eighth aspect.

The tenth aspect of the invention features an isolated cell, e.g., a mammalian cell, which expresses the polypeptide of any one of the first three aspects of the invention. In a desirable embodiment of the tenth aspect, the mammalian cell is a human cell. In additional desirable embodiments, the polypeptide is an antibody such as a monoclonal antibody or an IgM antibody.

In the eleventh aspect, the invention features a method of producing the purified polypeptide of any one of the first three aspects of the invention. This method involves contacting a cell with the vector of the eighth aspect and isolating the polypeptide expressed by the cell.

The twelfth aspect of the invention features use of the polypeptide of any one of the first three aspects of the invention in a method of diagnosing a neoplasm in a mammal, e.g., a human. This method involves the steps of, (a) contacting a cell or tissue sample derived from the mammal with the purified polypeptide of any one of the first three aspects of the invention, and (b) detecting whether the purified polypeptide binds to the cell or tissue sample, where binding of the purified polypeptide to the cell or tissue sample is indicative of the mammal having a neoplasm. In a desirable embodiment of the twelfth aspect, the cell or tissue is derived from a stomach, a colon, a lung, an esophagus, a pancreas, a urinary bladder, a kidney, a prostate, a female breast, an ovary, or a uterus. Desirably, the polypeptide used in the twelfth aspect of the invention is an antibody, such as a monoclonal antibody. In other desirable embodiments of the twelfth aspect, the polypeptide is conjugated to a detectable agent, for example, a radionuclide, a fluorescent marker, an enzyme, a cytotoxin, a cytokine, or a growth inhibitor. In addition, this detectable agent desirably is capable of inducing apoptosis of the cell. In further desirable embodiments of the twelfth aspect of the invention, the polypeptide is conjugated to a protein purification tag, such as a cleavable protein purification tag.

In the thirteenth aspect, the invention features a method of treating a proliferative disorder in a mammal, e.g., a human, using the purified polypeptide of any one of the first three aspects of the invention. This method involves the step of contacting a cell with the purified polypeptide of any one of the first three aspects of the invention, where binding of the purified polypeptide to the cell results in a reduction in proliferation of the cell. This proliferative disorder may be, for example, a diffuse-type stomach adenocarcinoma, an intestinal-type stomach adenocarcinoma, an adenocarcinoma of the colon, an adenocarcinoma of the lung, a squamous cell carcinoma of the lung, a squamous cell carcinoma of the esophagus, an adenocarcinoma of the pancreas, a urothel carcinoma of the urinary bladder, a renal cell carcinoma of the kidney, an adenocarcinoma of the prostate, an invasive ductal carcinoma of the breast, an invasive lobular carcinoma of the breast, an adenocarcinoma of the ovary, or an adenocarcinoma of the uterus. In desirable embodiments of the thirteenth aspect, the polypeptide is an antibody, for example, a monoclonal antibody.

In other desirable embodiments of the thirteenth aspect, the polypeptide is conjugated to a detectable agent selected from the group consisting of a radionuclide, a fluorescent marker, an enzyme, a cytotoxin, a cytokine, and a growth inhibitor. Desirably, this detectable agent is capable of inhibiting cell proliferation of the cell. In further desirable embodiments of this aspect of the invention, the polypeptide is conjugated to a protein purification tag, such as a cleavable protein purification tag.

In the fourteenth aspect, the invention features a medicament including the purified polypeptide of any one of the first three aspects of the invention in a pharmaceutically acceptable carrier and, in the fifteenth aspect, the invention features a diagnostic agent containing the purified polypeptide of any one of the first three aspects of the invention.

DEFINITIONS

By "detectable agent" is meant a compound that is linked to a diagnostic agent to facilitate detection. Such a "detectable agent" may be covalently or non-covalently linked to a diagnostic agent. In addition, the linkage may be direct or indirect. Examples of "detectable agents" include, protein purification tags, cytotoxins, enzymes, paramagnetic labels, enzyme substrates, co-factors, enzymatic inhibitors, dyes, radionuclides, chemiluminescent labels, fluorescent markers, growth inhibitors, cytokines, antibodies, and biotin.

By a "diagnostic agent" is meant a compound that may be used to detect a neoplastic cell by employing any one of the assays described herein as well as any other method that is standard in the art. A diagnostic agent may include, for example, an antibody which specifically binds to at least one of the following cells: lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), and lung squamous carcinoma cell line LOU-NH91 (DSMZ accession number ACC 393), but not to non-neoplastic cells. In addition, a "diagnostic agent" may inhibit cell proliferation, induce apoptosis, or both only when it is bound to a neoplastic cell, but not a non-neoplastic cell.

Examples of neoplastic cells that may be detected with such a "diagnostic agent" include stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, and adenocarcinoma of the uterus cells. Moreover, a "diagnostic agent" may include, for example, peptides, polypeptides, synthetic organic molecules, naturally-occurring organic molecules, nucleic acid molecules, and components thereof, as well as one or more detectable agent covalently or non-covalently linked to the diagnostic agent.

By a "functional fragment," as used herein in reference to polypeptide, is meant a fragment that retains at least one biological activity of the full-length polypeptide. Examples of such a biological activity are the ability to specifically bind an antigen, induce apoptosis, and/or inhibit cell proliferation. These biological activities may be determined, for example, using any one of the assays described herein.

Examples of functional fragments of an antibody are $V_L$, $V_H$, $F_V$, $F_C$, Fab, Fab', or F(ab')$_2$, fragments (see, e.g., Huston et al., Cell Biophys. 22:189-224, 1993; and Harlow and Lane, Using Antibodies: A Laboratory Manual, Cold Spring Harbor Laboratory Press, N.Y., 1999). Desirably, a "functional fragment" has an amino acid sequence that is substantially identical to a fragment, e.g., 3, 4, 5, 10, 15, 20, 15, 30, 50, 75, or 100 contiguous amino acids, of the amino acid sequence of SEQ ID NO:2. In more desirable embodiments, a "functional fragment" is identical to a fragment of the sequence of SEQ ID NO:2. Such a "functional fragment" may contain 3, 4, 5, 10, 15, 20, 15, 30, 50, 75, or 100 contiguous amino acids of SEQ ID NO:2, or may be the entire amino acid sequence of SEQ ID NO:2. In desirable embodiments, such a fragment includes one or more of the Complement Determining Regions (CDR) of the $V_H$ region of the LM-1 antibody. For example, a functional fragment may include 16-22, 37-52, and/or 85-103 of SEQ ID NO:2.

By "high stringency hybridization conditions" is meant, for example, hybridization at approximately 42° C. in about 50% formamide, 0.1 mg/ml sheared salmon sperm DNA, 1% SDS, 2×SSC, 10% Dextran Sulfate, a first wash at approximately 65° C. in about 2×SSC, 1% SDS, followed by a second wash at approximately 65° C. in about 0.1×SSC. Alternatively, "high stringency hybridization conditions" may include hybridization at approximately 42° C. in about 50% formamide, 0.1 mg/ml sheared salmon sperm DNA, 0.5% SDS, 5×SSPE, 1×Denhardt's, followed by two washes at room temperature in 2×SSC, 0.1% SDS, and two washes at between 55-60° C. in 0.2×SSC, 0.1% SDS.

A "hybridoma," as used herein, is any cell that is artificially created by the fusion of a normal cell such as an activated lymphocyte with a neoplastic cell, e.g., a myeloma. The hybrid cell, which results from the fusion of at least two cells, may produce a monoclonal antibody or T cell product identical to those produced by the immunologically-competent parent. In addition, these cells, like the neoplastic parent, are immortal.

"Inhibiting cell proliferation," as used herein, refers to a reduction in the rate of cell division of a cell in comparison with the normal rate of cell division of that type of cell. Inhibition of cell proliferation may be assayed using a number of methods standard in the art, for example, the MTT cell proliferation assay described herein, BrdU incorporation, and $^3$H thymidine uptake. Such assays are described, for example, in Ausubel et al., Current Protocols in Molecular Biology, Wiley Interscience, New York, 2001; and Sambrook et al., Molecular Cloning: A Laboratory Manual, 3$^{rd}$ edition, Cold Spring Harbor Laboratory Press, N.Y., 2001. Desirably, the inhibition of cell proliferation is 20%, 40%, 50%, or 75%. In desirable embodiments, the inhibition of cell proliferation is 80%, 90%, 95%, or even a complete inhibition of cell proliferation.

"Inducing apoptosis," as used herein, refers to the appearance of characteristics in a cell that are well defined in the art (see, e.g., Wyllie et al., Br. J. Cancer 80 Suppl. 1:34-37, 1999; Kerr et al., Br. J. Cancer 26:239-257, 1972). These characteristics include morphological characteristics, such as membrane blebbing, DNA condensation, as well as changes in F-actin content, mitochondrial mass, and membrane potential. The induction of apoptosis may be assayed using a number of methods standard in the art, for example, a cell death ELISA, TUNEL staining, DNA stains, e.g., Hoechst 33258, and staining with various vital dyes such as acridine orange, Mito Tracker Red® staining (Molecular Probes, Eugene, Oreg.), and Annexin V® staining (Becton Dickinson, NJ). As used herein "inducing apoptosis" refers to an increase in the number of cells undergoing apoptosis when compared with a control cell population. For instance, the increase of apoptosis may be 10%, 20%, 40%, 50%, or 75%. In desirable embodiments, the induction of apoptosis results in an increase of apoptosis that is 2-fold, 3-fold, 10-fold, or even 100-fold over that seen in a control cell population.

A "neoplastic cell," as used herein, refers to a cell which is undergoing cell division, not undergoing apoptosis, or both, under inappropriate conditions. For example, a "neoplastic cell" may undergo cell division when a corresponding non-neoplastic cell does not undergo cell division, or, alternatively, a "neoplastic cell" may not respond to normal cell-cycle checkpoint controls.

A "proliferative disease," as used herein, refers to any disorder that results in the abnormal proliferation of a cell. Specific examples of proliferative diseases are various types of neoplasms, such as stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, and adenocarcinoma of the uterus. However, proliferative diseases may also be the result of the cell becoming infected with a transforming virus.

A "protein purification tag," as used herein, is a peptide, e.g., an epitope tag, that is covalently or non-covalently added to a protein to aid in the purification of the protein. Desirably such peptides bind with high affinity to an antibody or to another peptide such as biotin or avidin. Commercially available examples of epitope tags include His-tags, HA-tags, FLAG®-tags, and c-Myc-tags. However, any epitope that is recognized by an antibody also may be used as a protein purification tag. See, for example, Ausubel et al., Current Protocols in Molecular Biology, Wiley Interscience, New York, 2001; and Sambrook et al., Molecular Cloning: A Laboratory Manual, 3' edition, Cold Spring Harbor Laboratory Press, N.Y., 2001. Protein purification tags may be cleaved from a protein, for example, by using an enzyme, e.g., thrombin, or a chemical, e.g., cyanogen bromide.

By "specifically recognizes" or "specifically binds," as used herein in reference to a polypeptide, e.g., an antibody, is meant an increased affinity of a polypeptide for a particular protein, e.g., an antigen, relative to an equal amount of any other protein. For example, an antibody, e.g., the LM-1 human monoclonal antibody, that specifically binds to lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), and lung squamous cell carcinoma cell line LOU-NH91 (DSMZ accession number ACC 393), cells desirably has an affinity for its antigen that is least 2-fold, 5-fold, 10-fold, 30-fold, or 100-fold greater than for an equal amount of any other antigen, including related antigens. Binding of a polypeptide to another polypeptide may be determined as described herein, and by any number of standard methods in the art, e.g., Western analysis, ELISA, or co-immunoprecipitation.

By "substantially identical" is meant a polypeptide or nucleic acid exhibiting at least 50%, 75%, 80%, 85%, or 90% identity to a reference amino acid (e.g., the sequence of SEQ ID NO:2) or nucleic acid sequence (e.g., the sequence of SEQ ID NO:1), or a fragment thereof. In desirable embodiments, the polypeptide or nucleic acid sequence is at least 95%, 98%, 99%, or even 100% identical to a reference amino acid or nucleic acid sequence. For polypeptides, the length of comparison sequences will generally be at least 3, 4, 5, 6, 8, 10, or 15 amino acids and desirably at least 20 or contiguous amino acids. In more desirable embodiments, the length of comparison sequences is at least 30, 50, 75, 90, 95, or 100 contiguous amino acids, or even the full-length amino acid sequence. For nucleic acids, the length of comparison sequences will generally be at least 9, 10, 15, 20, or 25 contiguous nucleotides, and desirably at least 30 contiguous nucleotides. In more desirable embodiments, the length of comparison sequences is at least 50, 75, 150, 225, 270, 285, or 300 contiguous nucleotides, or even the full-length nucleotide sequence.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Multiple sequences may also be aligned using the Clustal W (1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

By "purified" or "isolated" is meant separated from other components that naturally accompany it. Typically, a factor is substantially pure when it is at least 50%, by weight, free from proteins, antibodies, and naturally-occurring organic molecules with which it is naturally associated, or in reference to a nucleic acid molecule, is free from the nucleic acid sequences that naturally flank the sequence of the nucleic acid molecule in the genome of an organism. Desirably, the factor is at least 75%, more desirably, at least 90% or 95%, and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques, such as those described by Ausubel et al. (*Current Protocols in Molecular Biology*, Wiley Interscience, New York, 2001). The factor is desirably at least 2, 5, or 10 times as pure as the starting material, as measured using polyacrylamide gel electrophoresis, column chromatography, optical density, HPLC analysis, or Western analysis (Ausubel et al., *Current Protocols in Molecular Biology*, Wiley Interscience, New York, 2001). Desirable methods of purification include immunoprecipitation, column chromatography such as immunoaffinity chromatography and nickel affinity columns, magnetic bead immunoaffinity purification, and panning with a plate-bound antibody.

By "vector" or "expression vector" is meant an expression system, a viral vector, a nucleic acid-based shuttle vehicle, a nucleic acid molecule adapted for nucleic acid delivery, or an autonomous self-replicating circular DNA (e.g., a plasmid). When a vector is maintained in a host cell, the vector can either be stably replicated by the cell during mitosis as an autonomous structure, incorporated into the genome of the host cell, or maintained in the host cell's nucleus or cytoplasm.

Other features and advantages of the invention will be apparent from the following Detailed Description, the Drawings, and the Claims.

BRIEF DESCRIPTION OF THE DRAWINGS

FIG. 1A shows staining of a squamous cell carcinoma of the lung; FIG. 1B shows staining of an adenocarcinoma of the colon; FIG. 1C shows staining of an esophageal squamous cell carcinoma; and FIG. 1D shows staining of an invasive ductal carcinoma of the breast. The original magnification for these images was 200×.

FIG. 2 shows the concentration dependent inhibition of cell proliferation with antibodies LM-1 on lung pancreas carcinoma cell line LOU-NH91. The control for these experiments was depleted cell culture supernatant with an unrelated IgM antibodies added at similar concentrations.

FIG. 4 shows LM-1 monoclonal antibody-induced apoptosis of lung carcinoma cell line LOU-NH91. The control in these experiments was depleted cell culture supernatant at a similar concentration.

FIG. 7 is the nucleic acid sequence (SEQ ID NO:1) and the amino acid sequence (SEQ ID NO:2) of the variable region of the heavy chain of human monoclonal antibody LM-1. Complement Determining Regions (CDR) 1-3 and the D and J regions are also shown.

DETAILED DESCRIPTION

Figure 1:
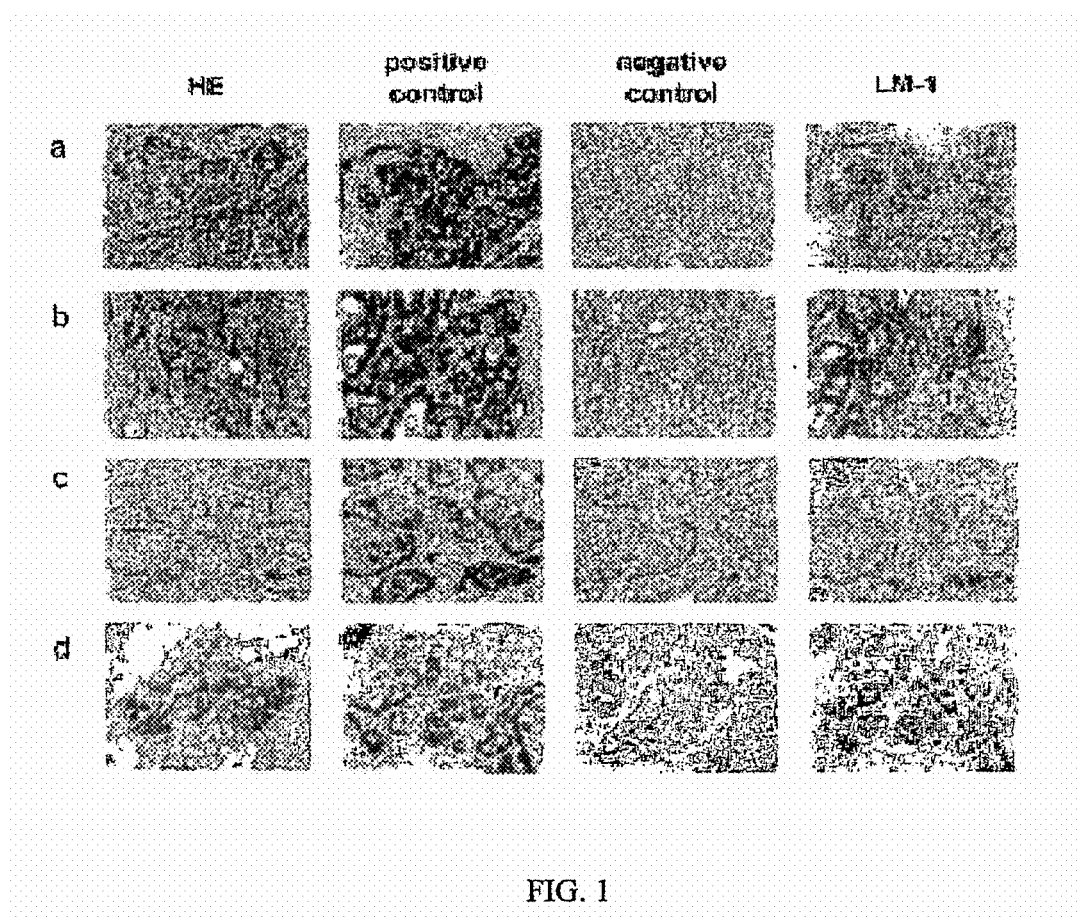
FIGS. 1A-1D are a series of images showing immunohistochemical staining of monoclonal antibody LM-1 on different carcinomas. Paraffin sections were stained with hematoxylin-eosin, positive control antibodies (CK5/6 for squamous cell carcinoma of the lung and esophagus, AE1/AE3 for adenocarcinoma of the colon, and CK8 for invasive ductal adenocarcinoma of the breast), secondary antibody alone as a negative control, and antibody LM-1.

The present invention features polypeptides, such as antibodies, and their use in the treatment and diagnosis of neoplasms. We have characterized human monoclonal antibody (LM-1) that specifically recognizes a number of carcinomas. Not only does this monoclonal antibody recognize these neoplasms, but, upon binding to a cell, it can induce apoptosis of neoplastic cells, inhibit their proliferation, or even both. Thus, the LM-1 monoclonal antibody, and other antibodies, or fragments thereof, that are specific for the antigen recognized by this antibody, may be used in a variety of methods for diagnosing and treating a neoplasm.

The cell line that produces the human LM-1 monoclonal antibody was deposited on Nov. 6, 2003 at the German Collection of Microorganisms and Cell Cultures ("DSMZ"— Deutsche Sammlung von Mikroorganismen and Zellkulturen GmbH, Mascheroder Weg 1b, 38124 Braunschweig, Germany) under the terms of the Budapest Treaty and has been assigned Accession Number DSM ACC2623.

Antibodies and Polypeptides

Antibodies play an essential role in maintaining the health of an individual. In particular, antibodies are present in serum and bind to and help eliminate diverse pathogens such as bacteria, viruses, and toxins. Antibodies consist of Y-shaped protein structures built from two heavy chains and two light chains. Each chain has a modular construction: each light chain consists of two domains, and each heavy chain has at least four domains The antigen binding site is fashioned by one domain from the heavy chain ($V_H$ domain) and one domain from the light chain ($V_L$ domain). Indeed, small antigen binding fragments can be prepared by linking these two domains, either associated non-covalently, or covalently via disulphide bonds or a peptide linker. The antigen binding domains are more variable in amino acid sequence than the other domains of the antibody, and are therefore termed variable (V) domains, in contrast to the constant (C) domains. The constant domains of the antibody are responsible for triggering antibody effector mechanisms, such as complement lysis and cell-mediated killing.

Antibodies are made by B-lymphocytes in a process involving gene rearrangement. During the development of these cells, the genes encoding the variable domains are assembled from genetic elements. In the case of the $V_H$ domains there are three elements, the un-rearranged $V_H$ gene, D segment, and $J_H$ segment. In the case of the $V_L$ domains, there are two elements, the un-rearranged $V_L$ (V Lambda or V Kappa) gene and the $J_L$ (J Lambda or J Kappa) segment. Random combination of these gene segments and random combination of the rearranged $V_H$ and $V_L$ domains generate a large repertoire of antibodies, capable of binding to a large diversity of equally diverse antigens. Further, the $V_H$ and $V_L$ regions each have three Complement Determining Regions (CDR) and four framework regions (FR). The FRs are the backbone of the antibody and the CDRs are the parts of the antibody that bind the antigen. One skilled in the art can determine the FR and CDR regions of an antibody by comparing the amino acid sequence of a number of antibodies raised in the same species.

In general, the presently claimed polypeptide is any agent that binds to any one of lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), and lung squamous cell carcinoma cell line LOU-NH91 (DSMZ accession number ACC 393), but does not bind to non-neoplastic cells. The polypeptide may be an antibody, such as a human monoclonal antibody (e.g., LM-1 or a functional fragment thereof). Overall, the polypeptide of the invention can exclusively bind to both neoplastic tissues and neoplastic cells, but not to non-neoplastic tissue or cells. The polypeptide also may induce apoptosis of a neoplastic cell to which it binds, but not in a non-neoplastic cell, or, alternatively, the polypeptide may inhibit proliferation of the neoplastic cell it binds to, but not in a non-neoplastic cell. Desirably, the polypeptide can simultaneously induce apoptosis and inhibit proliferation of neoplastic cells, but not of non-neoplastic cells. Such a polypeptide is, therefore, useful for the detection, monitoring, prevention, and treatment of cancers in mammals. Exemplary cancers amenable to the methods of the current invention include colorectal cancer, ovarian carcinoma, squamous cell lung carcinoma, small cell lung carcinoma, lobular and ductal mammary carcinomas, melanoma, breast cancer, lung cancer, such as lung adenocarinomas, gastric cancer, pancreatic cancer, such as pancreatic adenocarcinomas, glioma, sarcomas, gastrointestinal cancer, brain tumor, esophageal cancer, such as esophagial squamous cell carcinomas, stomach cancer, osteosarcoma, fibrosarcomas, urinary bladder cancer, prostate cancer, such as prostate adenocarcinomas, renal cancer, ovarian cancer, testicular cancer, endometrial cancer, cervical cancer, uterine adenocarcinomas, Hodgkin's disease, lymphomas, and leukemias. Such polypeptides are particularly useful for the detection and treatment of a stomach adenocarcinoma, colorectal adenocarcinoma, squamous cell lung carcinoma, lung adenocarinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, or adenocarcinoma of the uterus.

Production

The polypeptides according to the claimed invention can be produced by any method known in the art for small scale, large scale, or commercial production of polypeptides. For example, monoclonal antibodies, such as LM-1, may be produced by hybridoma cell lines. Such cell lines are typically generated by the fusion of spleen and lymph node lymphocytes derived from patients having a neoplasm, such as colon carcinoma or a pancreatic carcinoma, with a heteromyeloma cell line. Exemplary heteromyeloma cell lines include, for example, HAB-1 (Vollmers et al, *Cancer* 74:1525-1532, 1994), CB-F7 (Delvig et al., *Hum. Antibodies Hybridomas* 6:42-46, 1995), K6H6B5 (Delvig et al., *Hum. Antibodies Hybridomas* 6:42-46, 1995), H7NS.934 (Delvig et al., *Hum. Antibodies Hybridomas* 6:42-46, 1995), SHM-D33 (Bron et al., Proc. Natl. Acad. Sci. USA 81:3214-3217, 1984), and B6B11 (Borisova et al., *Vopr. Virusol.* 44:172-174, 1999). The ability to generate human monoclonal antibodies from lymphocytes of cancer patients allows the isolation of antibodies that are generated by an immune response in the cancer patient to the tumor.

Typically, portions of the lymph nodes or spleen are surgically removed from a patient having cancer, such as colon carcinoma or a pancreatic carcinoma. Lymphocytes may be prepared as cell suspensions by mechanical means and subsequently fused at, for example, a 1:2 or 1:3 ratio with a heteromyeloma cell line under conditions that result in cell fusion. For instance, the heteromyeloma cell line HAB-1, which is generated by the fusion of a human lymphocyte with the mouse myeloma NS-0, may be used for this purpose. A proportion of lymphocytes isolated from the cancer patient may also be maintained in culture. These cells serve as a source of human autologous cells useful for the initial antibody screening described below.

Following the fusion of the lymphocytes derived from the cancer patient with the heteromyeloma cell line, an antibody producing hybridoma or trioma is generated. Once constructed, hybridomas are generally stable in growth and antibody production in standard and mass cultures (flasks, miniPerm, fermenters, etc.) for several months. Levels of antibody production typically range between 0.01-0.1 mg/mL in flasks and between 0.1-0.5 mg/mL in miniPerm. Cell fusion may be achieved by any method known in the art, and includes, for example, the use of 40% polyethylene glycol. Hybridomas may be cultured in media containing HAT (Hypovanthin-aminopterin-thymidine) and after four weeks, supernatants may be screened for antibody production using an ELISA assay. Positive clones may then be tested in attachment inhibition and binding assays using autologous cell lines as prepared above. Positive clones further may be tested using immunoperoxidase staining of tumor and normal tissues. Thus, clones may be selected on the basis of their reactivity with autologous and allogeneic neoplastic cells. The antibody may be purified from mass cultures with use of cation-exchange chromatography followed by gel filtration as described, for example, by Vollmers et al. (Oncology Reports 5:35-40, 1998). Following the production of antibodies, additional functional and immunohistochemical tests of the antibodies produced by the trioma may be performed. For example, the antibodies produced by the hybridoma can be tested for their ability to induce apoptosis, inhibit cellular proliferation, or both, relative to untreated control cells. The antibodies can also be tested for their ability to specifically bind the neoplastic cell lines e.g., lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), and lung squamous cell carcinoma cell line LOU-NH91 (DSMZ accession number ACC 393), relative to non-neoplastic cells.

Alternatively, the polypeptide, including an antibody, or a fragment thereof, may be produced by the expression of the polypeptide or antibody in a host cell such as $E.$ $coli$ or yeast, e.g., $S.$ $cerevisiae$, or a mammalian cell line. For example, an antibody of the invention may be identified as follows. A nucleic acid sequence encoding an antibody, or a fragment thereof, may be inserted into filamentous bacteriophage to generate libraries of approximately $10^7$ or more antibodies. Each phage expresses an antibody on its surface that is encoded by the nucleic acid it contains. Antibodies of the invention may thus be screened and detected by functional and histochemical assays as described herein, and such genes may be subsequently selected and expressed in $E.$ $coli$. This system is described, for example, in U.S. Pat. No. 5,876,691.

Antibodies, or functional fragments thereof, may also be generated using, for example, direct synthesis using recombinant methods. These methods are standard in the art. For example, a nucleic acid sequence may be amplified using the polymerase chain reaction (PCR). The PCR technique is known in the art and is described, for example in U.S. Pat. No. 4,683,195. Using standard methods, and as described herein, the sequence of a monoclonal antibody expressed by a hybridoma may be obtained and functional fragments of the antibody may be amplified. For example, whole RNA may be isolated from a hybridoma expressing a tumor-specific monoclonal antibody. cDNA may then be generated from the RNA using reverse transcriptase and the cDNAs which contain the functional fragments of the variable regions of the heavy and light chains may be amplified using PCR. The PCR products may then be purified and cloned into expression vectors, e.g., plasmid or viral vectors. Many standard vectors are available and the selection of the appropriate vector will depend on, for example, the size of the DNA inserted into the vector and the host cell to be transfected with the vector.

The nucleic acid molecules of the invention may be expressed in a variety of standard vectors and host cells. Any promoter that is active in the host cell may be used to express a nucleic acid molecule. Nonetheless, for expression of an antibody or a fragment of an antibody in a mammalian cell, use of an immunoglobulin gene promoter is desirable. Methods of introducing a vector into a host cell are standard in the art and include, electroporation, use of synthetic lipid polymers, e.g., Lipofectin™, use of calcium chloride, and use of DEAE Dextran. Such methods are also described in, for example, Ausubel et al., $Current$ $Protocols$ $in$ $Molecular$ $Biology$, Wiley Interscience, New York, 2001; and Sambrook et al., $Molecular$ $Cloning$: $A$ $Laboratory$ $Manual$, $3^{rd}$ edition, Cold Spring Harbor Laboratory Press, N.Y., 2001.

Isolation of Amino Acid Variants of a Polypeptide

Amino acid sequence variants of a polypeptide, such as an antibody, e.g., an LM-1 antibody, can be prepared by introducing appropriate nucleotide changes into the DNA encoding the antibody, or by in vitro synthesis of the desired polypeptide. Such variants include, for example, deletions from, or insertions or substitutions of, residues within the amino acid sequence of the LM-1 antibody. Any combination of deletion, insertion, and substitution can be made to arrive at the final construct, provided that the final construct possesses the desired characteristics, e.g., the ability to induce apoptosis of a neoplastic cell, but not a non-neoplastic cell, or the ability to inhibit the proliferation of a neoplastic cell, but not a non-neoplastic cell. The amino acid changes also may alter post-translational processes of an antibody, such as changing the number or position of glycosylation sites, altering the membrane anchoring characteristics, or modifying its susceptibility to proteolytic cleavage.

In designing amino acid sequence variants of a polypeptide, such as an antibody, the location of the mutation site and the nature of the mutation will depend on characteristic(s) to be modified. The sites for mutation can be modified individually or in series, e.g., by substituting first with conservative amino acid choices and then with more radical selections depending upon the results achieved, or deleting the target residue.

A useful method for identification of specific residues or regions for mutagenesis in a polypeptide is called "alanine scanning mutagenesis" and is described, for example, by Cunningham and Wells (Science 244:1081-1085, 1989). Here, a residue or group of target residues are identified (e.g., charged residues such as arg, asp, his, lys, and glu) and replaced by a neutral or negatively charged amino acid (most desirably alanine or polyalanine) to affect the interaction of the amino acids with the surrounding aqueous environment in or outside the cell. The domains demonstrating functional sensitivity to the substitutions then are refined by introducing further or other variants at or for the sites of substitution. Thus, while the site for introducing an amino acid sequence variation is predetermined, the nature of the mutation need not be predetermined. For instance, to optimize the performance of a mutation at a given site, alanine scanning or random mutagenesis may be conducted at the target codon or region and the expressed variants are screened for, e.g., the ability to induce apoptosis of a neoplastic cell and not a non-neoplastic cell, or to inhibit the proliferation of a neoplastic cell and not a non-neoplastic cell.

The sites of greatest interest for substitutional mutagenesis include sites identified as affecting the biological activity of a polypeptide. These sites, especially those falling within a sequence of at least three other identically conserved sites, may be substituted in a relatively conservative manner. For instance, ala may be substituted with val, leu, or ile; arg may be substituted with lys, gin, or asn; asn may be substituted with gin, his, lys, or arg; asp may be substituted with glu; cys may be substituted with ser; gin may be substituted with asn; glu may be substituted with asp; gly may be substituted with pro; his may be substituted with asn, gin, lys, or arg; ile may be substituted with leu, val, met, ala, or phe; leu may be substituted with ile, val, met, ala, or phe; lys may be substituted with arg, gin, or asn; met may be substituted with leu, phe, or ile; phe may be substituted with leu, val, ile, or ala; pro may be substituted with gly; ser may be substituted with thr; thr may be substituted with ser; trp may be substituted with tyr; tyr may be substituted with trp, phe, thr, or ser; and val may be substituted with ile, leu, met, or phe.

Conjugation of the Antibody with a Detectable Agent

If desired, the claimed polypeptide such as an antibody (e.g., monoclonal antibody LM-1), or a functional fragment thereof, may be linked to a detectable agent to facilitate the purification of the polypeptide as well as the diagnosis, monitoring, or treatment of cancer in a mammal in need thereof. The selection of suitable detectable agent will depend on the intended use of the polypeptide and will be apparent to those of ordinary skill in the art. Detectable agents according to the claimed invention include, for example, protein purification tags, cytotoxins, enzymes, paramagnetic labels, enzyme substrates, co-factors, enzyme inhibitors, dyes, radionuclides, chemiluminescent labels, fluorescent markers, growth inhibitors, and biotin.

A protein purification tag may be conjugated to the polypeptide of the invention, to facilitate isolation of the polypeptide. Examples of tags that can be used include His-tags, HA-tags, FLAG®-tags, and c-Myc tags. An enzymatic or chemical cleavage site may be engineered between the polypeptide and the tag moiety so that the tag can be removed following purification. Suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Examples of suitable radioisotopic labels include $^{3}$H, $^{125}$I, $^{131}$I, $^{32}$P, $^{35}$S, and $^{14}$C. Desirably, the radioisotope will emit in the 10-5,000 kev range, more desirably 100-500 kev. Paramagnetic isotopes may also be conjugated to the polypeptide and used in vivo for the diagnosis and treatment of cancer. The use of such conjugated antibodies may be for in vivo nuclear magnetic resonance imaging. Such a method has previously been described (see, for example, Schaefer et al., JACC 14:472-480, 1989; Shreve et al., Magn. Reson. Med. 3:336-340, 1986; Wolf, Physiol. Chem. Phys. Med. NMR 16:93-95, 1984; Wesbey et al., Physiol. Chem. Phys. Med. NMR 16:145-155, 1984; and Runge et al., Invest. Radiol. 19:408-415, 1984). Alternatively, the radiolabeled antibody may also be used in radioimmunoguided surgery (RIGS), which involves the surgical removal of any tissue the labeled antibody binds to. Thus, the labeled antibody guides the surgeon towards neoplastic tissue by distinguishing it from non-neoplastic tissue. Radiolabels useful for tumor imaging are preferably short-lived radioisotopes. Various radioactive metals with half-lives ranging from 1 hour to 11.4 days are available for conjugation to antibodies, such as scandium-47 (3.4 days), gallium-67 (2.8 days), gallium-68 (68 minutes), technetium-99m (6 hours), indium-111 (3.2 days), and radium-223 (11.4 days), of which gallium-67, technetium-99m, and indium-111 are preferable for gamma camera imaging, gallium-68 is preferable for positron emission tomography, and scandium-47 and radium-223 (and other alpha-emitting radionuclides) are preferable for tumor therapy.

Examples of suitable fluorescent markers include fluorescein, isothiocyalate, rhodamine, phycoerythrin, phycocyanin, allophycocyanin, ophthaldehyde, and fluorescamine. Examples of chemiluminescent markers include a luminal label, isoluminal label, aromatic acridinium ester label, imidazole label, acridinium salt label, oxalate ester label, luciferin label, luciferase label, and aequorin label. Those of ordinary skill in the art would know of other suitable labels, which may be employed in accordance with the present invention. Conjugation of these detectable agents to the claimed polypeptides such as monoclonal antibodies, or fragments thereof, can be accomplished using standard techniques commonly known in the art. Typical antibody conjugation techniques are described by Kennedy et al. (*Clin. Chim. Acta* 70, 1-31, 1976) and Schurs et al. (*Clin. Chim. Acta* 81, 1-40, 1977) and include, for example, the glutaraldehyde method, the periodate method, the dimaleimide method, the m-maleimidobenzyl-N-hydroxy-succinimide ester method. Antibodies may be radiolabeled by any of several techniques known to the art, described, for example, in U.S. Pat. No. 4,444,744. All of these methods are incorporated by reference herein.

In all aspects of the present invention, it is understood that mixtures of different or the same labeled polypeptides specific to different antigens or different epitopes of the same antigen associated with the same or different tumor or tumor cell types may be used. Such a combination may enhance detection, localization and/or therapy in certain cases, and can also increase the range of a broad screen for more than one neoplasm or type of neoplasm.

Polypeptides Conjugated to Anti-Tumor Agents

Although the polypeptide of the invention may induce apoptosis of neoplastic cells, inhibit cellular proliferation of neoplastic cells, or both, the polypeptide may in addition be conjugated to an agent that kills neoplastic cells or that inhibits their proliferation. The targeting ability of the polypeptide, such as an antibody or fragment thereof, results in the delivery to deliver of the cytotoxic or anti-proliferative agent to the tumor to enhance the destruction of the tumor. The polypeptide therefore may be used for the treatment and prevention of cancer in a mammal, such as a human patient. The cytotoxic agent linked to the polypeptide may be any agent that destroys or damages a tumor cell or tumor to which the polypeptide has bound. Examples of such agents include chemotherapeutic agents or radioisotopes, enzymes which activates a pro-drug, or a cytokine.

Suitable chemotherapeutic agents are known to those skilled in the art and include, for example, taxol, mithramycin, deoxyco-formycin, mitomycin-C, L-asparaginase, interferons (especially IFN-alpha), etoposide, teniposide, anthracyclines (e.g., daunomycin and doxorubicin), methotrexate, vindesine, neocarzinostatin, cis-platinum, chlorambucil, cytosine arabinoside, 5-fluorouridine, melphalan, ricin, and calicheamicin. The chemotherapeutic agents may be conjugated to the antibody using conventional methods known in the art.

Suitable radioisotopes for use as cytotoxic agents are also known to those skilled in the art and include, for example, $^{131}$I, or an astatine such as $^{211}$At. These isotopes may be attached to the polypeptide, either covalently or non-covalently, using conventional techniques known in the art.

Alternatively, the cytotoxic agent may also be an enzyme, which activates a pro-drug. This allows the conversion of an inactive pro-drug to its active, cytotoxic form at the tumor site and is called "antibody-directed enzyme pro-drug therapy" (ADEPT). Thus, the polypeptide-enzyme conjugate may be administered to the patient and allowed to localize in the region of the tumor to be treated. The pro-drug is then administered to the patient such that conversion to the cytotoxic drug is localized in the region of the tumor to be treated under the influence of the localized enzyme. An exemplary enzyme is bacterial carboxypeptidase G2 (CPG2) the use of which is described in, for example, WO 88/07378. The polypeptide-enzyme conjugate may, if desired, be modified in accordance with the teaching of WO 89/00427, such as to accelerate its clearance from areas of the body that are not in the vicinity of a neoplasm. The polypeptide-enzyme conjugate may also be used in accordance with WO 89/00427, for example, by providing an additional component, which inactivates the enzyme in areas of the body that are not in the vicinity of the tumor.

As another alternative, the cytotoxic agent conjugated to the claimed polypeptide may also be a cytokine such as interleukin-2 (IL-2), interleukin-4 (IL-4), or tumor necrosis factor alpha (TNF-alpha). The polypeptide targets the cytokine to the tumor so that the cytokine mediates damage to or destruction of the tumor without affecting other tissues. The cytokine may be fused to the polypeptide at the DNA level using conventional recombinant DNA techniques.

In addition, any inhibitor of cell proliferation. e.g., genistein, tamoxifen, or cyclophosphamide, may be conjugated with a polypeptide of the invention.

Dosage

With respect to the therapeutic methods of the invention, it is not intended that the administration of the claimed polypeptide to a patient be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to decrease the number of neoplastic cells by inducing apoptosis of neoplastic cells, by inhibiting proliferation of tumor cells, or both. The compound(s) may be administered to the patient in a single dose or in multiple doses. When multiple doses are administered, the doses may be separated from one another by, for example, one day, two days, one week, two weeks, or one month. For example, the polypeptide (e.g., monoclonal antibody LM-1, or a functional fragment thereof) may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. The precise dose will vary dependent on the polypeptide used, the density, on the tumor surface, of the ligand to which the polypeptide binds, and the rate of clearance of the polypeptide. For example, the dosage of the LM-1 antibody can be increased if the lower dose does not provide sufficient anti-neoplastic activity. Conversely, the dosage of the LM-1 antibody can be decreased if the neoplasm is cleared from the patient.

While the attending physician ultimately will decide the appropriate amount and dosage regimen, a therapeutically effective amount of the claimed polypeptide, such as a monoclonal antibody or a fragment thereof, may be, for example, in the range of about 0.1 mg to 50 mg/kg body weight/day or 0.70 mg to 350 mg/kg body weight/week. Desirably a therapeutically effective amount is in the range of about 0.50 mg to 20.0 mg/kg, and more desirably in the range of about 0.50 mg to 15.0 mg/kg for example, about 0.2, 0.3, 0.5, 1.0, 1.5, 2.0, 2.5, 3.0, 3.5, 4.0, 4.5, 5.0, 5.5, 6.0, 7.0, 8.0, 8.5, 9.0, 10.0, 11.0, 12.0, 13.0, 14.0, or 15.0 mg/kg body weight administered daily, every other day, or twice a week.

For example, a suitable dose is an amount of the polypeptide that, when administered as described above, is capable of inducing apoptosis, and is at least 20% above the basal (i.e., untreated) level. In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. According to this invention, the administration of the polypeptide can induce neoplastic cell apoptosis by at least 20%, 40%, 50%, or 75% above that of an untreated control as measured by any standard assay known in the art. More desirably, apoptosis is induced by 80%, 90%, 95%, or even 100% above that of an untreated control. Alternatively, the administration of the polypeptide can inhibit neoplastic cell proliferation by at least 20%, 40%, 50%, or 75% below that of an untreated control as measured by any standard assay known in the art. More desirably, proliferation is inhibited by 80%, 90%, 95%, or even 100% below that of an untreated control. Most desirably, the polypeptide can simultaneously inhibit proliferation and induce apoptosis of neoplastic cells relative to untreated control cells. Such responses can be monitored by any standard technique known in the art. In general, for pharmaceutical compositions, the amount of antibody present in a dose ranges from about 25 µg to 5 mg per kg of host. Suitable dose sizes will vary with the size of the patient, but will typically range from about 0.1 mL to about 5 mL.

Formulation of Pharmaceutical Compositions

The claimed polypeptide may be administered by any suitable means that results in a concentration having anti-neoplastic properties upon reaching the target region. The polypeptide may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The pharmaceutical composition may be administered parenterally by injection, infusion or implantation (subcutaneous, intravenous, intramuscular, intraperitoneal, or the like) in dosage fauns, formulations, or via suitable delivery devices or implants containing conventional, non-toxic pharmaceutically acceptable carriers and adjuvants. If the neoplastic cells are in direct contact with the blood (e.g., leukemias), or if the tumor is only accessible by the bloodstream then the intravenous (I.V.) route may be used. In cases in which tumors grow in confined spaces such as the pleural cavity or the peritoneal cavity, the polypeptide may be directly administered into the cavity rather than into the blood stream. The formulation and preparation of such compositions are well known to those skilled in the art of pharmaceutical formulation. Formulations can be found in Remington: The Science and Practice of Pharmacy, supra.

Diagnosis and Monitoring Cancer Progression

As discussed above, the present invention is directed to a method for detecting or diagnosing a neoplasm in a mammal, preferably a human patient. Typically, any neoplasm in which administration of the claimed polypeptide causes an induction in apoptosis or a reduction in proliferation are amenable to the methods of this invention.

The claimed polypeptides are particularly useful since they are specific to neoplasms or neoplastic cells, but not normal cells or tissue. Accordingly, this polypeptide can bind to neoplastic cells within the tumor, but not the normal surrounding tissue, thus allowing the detection, the treatment, or both, of a neoplasm in a mammal. For instance, one may use a polypeptide of the invention to determine is a biopsy removed the entire tumor by verifying that no cells bound by the polypeptide remain in the patient or, by verifying that tumor removed from the patient is entirely surrounded by cells that are not bound by the polypeptide.

It is understood that to improve the sensitivity of detection, multiple neoplastic markers may be assayed within a given sample or individual. Thus, polypeptides such as antibodies or functional fragments specific for different antigens may be combined within a single assay, or in multiple assays. Further, multiple primers or probes specific to neoplasms may be used concurrently. The selection of markers may be based on routine experiments to determine combinations that results in optimal sensitivity.

In Vitro Detection of a Neoplasm

In general, the diagnosis of a neoplasm in a mammal involves obtaining a biological sample from the mammal (e.g., human patient), contacting such sample with the polypeptide of the invention (e.g., a monoclonal antibody, such as LM-1, or a functional fragment thereof), detecting in the sample the level of reactivity or binding of the polypeptide to neoplastic cells relative to a control sample, which corresponds to non-neoplastic cells derived from healthy tissue from the mammal in which the cancer is being diagnosed or from another patient known not to have neoplasm. Thus, the methods of this invention are particularly useful for the detection of early stage tumors or metastases, which are otherwise undetectable. Accordingly, in addition to diagnosing a neoplasm in a patient, the methods of this invention may also be used to monitor progression of a neoplasm in a mammal. The polypeptides described herein therefore may be used as markers for the progression of a neoplasm. For this purpose, the assays described below, which are used for the diagnosis of a neoplasm, may be performed over time, and the change in the level of reactive polypeptide(s) evaluated. For example, the assays may be performed every 24-72 hours for a period of 6 months to 1 year, and thereafter performed as needed. In general, a neoplasm is progressing in those patients in whom the level of bound polypeptide detected increases over time. In contrast, the neoplasm is not progressing when the level of bound polypeptide either remains constant or decreases with time. Alternatively, as is noted above, the polypeptide of the invention may be used to determine the presence of tumor cells in the mammal following tumor resection by surgical intervention to determine whether the tumor has been completely removed from the mammal.

Desirably, the polypeptide is linked to a detectable agent, which facilitates detection, or measurement of polypeptide reactivity. The biological sample is any biological material, which may contain neoplastic cells and include, for example, blood, saliva, tissue, serum, mucus, sputum, urine, or tears. The biological sample may also be a tissue section, which may be fixed tissue, fresh tissue, or frozen tissues. A neoplasm is detected or diagnosed in the mammal from which the sample was obtained if there is an increase in the level of reactivity of the antibody with the biological sample over the control sample. Such increase is at least 10%, 20%, 30%, 40%, 50%, or more than 50% over control levels. The level of binding or reactivity can be determined by any method known in the art and is described in further detail below.

In Vitro Diagnostic Assays

The diagnosis of neoplasms using the claimed polypeptide may be performed by any method known to those of ordinary skill in the art for using a binding agent to detect polypeptide markers in a sample. See, e.g., Harlow and Lane, Using Antibodies: A Laboratory Manual, Cold Spring Harbor Laboratory Press, N.Y., 1999. For example, the polypeptide may be used for enzyme-linked immunosorbent assay (ELISA), Western blotting or in situ detection of tumor cells in a tissue sample. For example, the ELISA assay typically involves the use of the polypeptide, such as an antibody, immobilized on a solid support to bind to the tumor cells in the biological sample. The bound tumor cell may then be detected using a detection reagent that contains a reporter group and that specifically binds to the antibody/tumor cell complex. Such detection reagents include, for example, any binding agent that specifically binds to the antibody, such as an anti-immunoglobulin, protein G, protein A, or a lectin. Alternatively, a competitive assay may be utilized, in which the polypeptide is an antibody and in which the antigens, to which the antibody is specific to is labeled with a reporter group and allowed to bind to the immobilized antibody after incubation of the antibody with the biological sample. The extent to which components of the sample inhibit the binding of the labeled antigens to the antibody is indicative of the reactivity of the sample with the immobilized antibody. Diagnosis of a neoplasm in a patient may also be determined by a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group. For example, to determine the presence or absence of a neoplasm, such as colorectal adenocarcinoma, the signal detected from the reporter group that remains bound to the solid support is generally compared to a signal that corresponds to a predetermined cut-off value. The cut-off value for the detection of a neoplasm is the average mean signal obtained when the antibody is incubated with samples from patients without a neoplasm.

The method employed for detecting the reporter group depends upon the nature of the reporter group. For radioactive groups, scintillation counting or autoradiographic methods may be used. Spectroscopic methods may be used to detect dyes, luminescent groups and fluorescent groups. Biotin may be detected using avidin, coupled to a different reporter group (commonly a radioactive or fluorescent group or an enzyme).

Enzyme reporter groups may generally be detected by the addition of substrate (generally for a defined period of time), followed by spectroscopic or other analysis of the reaction products.

The polypeptides of the invention may also be employed histologically for in situ detection or quantitative determination of tumor cells, for example, by immunofluorescence or immunoelectron microscopy. In situ detection or determination may be accomplished by removing a tissue specimen from a patient and allowing a labeled antibody to bind to any tumor cell in the specimen. Using such a procedure not only allows the detection of neoplastic cells in a sample, but also allows for the determination of their spatial distribution. As another example, the biological sample can be a smear of biological material containing neoplastic cells on a slide, and the detection of neoplastic cells in the biological material is achieved by examining the smear with a microscope or by fluocytometry.

In Vivo Detection of a Neoplasm

Alternatively, the antibody of the invention may also be used in vivo for detecting and localizing a neoplasm. Such a method may involve injecting a mammal, desirably a human subject, parenterally with a polypeptide of the invention, such as monoclonal antibody LM-1, or a functional fragment thereof, which has been labeled with a detectable agent, and is described, for instance, in U.S. Pat. No. 4,444,744. For example, the polypeptide can be radiolabeled with a pharmacologically inert radioisotope and administered to the patient. The activity of the radioisotope can be detected in the mammal using a photoscanning device, and an increase in activity relative to a control reflects the detection and localization of a neoplasm.

Treatment

In addition to the diagnosis and monitoring of neoplasms in mammals, the present invention also features methods for treating neoplasms in a mammal, desirably a human patient. The method generally involves the administration of a biologically effective amount of the polypeptide of the invention to the patient. The polypeptide is typically administered to the mammal by means of injection using any routes of administration such as by intrathecal, subcutaneous, submucosal, or intracavitary injection as well as for intravenous or intraarterial injection. Thus, the polypeptide may be injected systemically, for example, by the intravenous injection of the polypeptide such as monoclonal antibody LM-1, or a functional fragment thereof, into the patient's bloodstream or alternatively, the polypeptide can be directly injected at the site of the neoplasm or at a location in proximity to the neoplastic cells.

In general, and as discussed above, binding of the polypeptide of the invention to neoplastic cells results in an induction in apoptosis, a reduction in cellular proliferation, or both relative to the control sample. Alternatively, the antibodies may also activate the complement pathway, which ultimately causes holes to be punctured into the cellular membrane, resulting in cell death.

If desired, the polypeptides may also be conjugated to drugs or toxins as described above. Once attached to the cell surface, the conjugate may be engulfed into the cell cytoplasm where cell enzymes cleave, and, thus, activate or free the drugs or toxins from the conjugate. Once released, the drugs or toxins damage the cell and irreversibly induce cell death. With respect to radiolabeled antibodies, binding to neoplastic cells and the resulting emission of radiation, at a short distance from the cell DNA, produces damage to the latter thus inducing cell death in the next replication round. For example, after a neoplasm has been detected and localized in a subject, a higher dose of labeled antibody, generally from 25 to 250 mCi for $^{131}$I, and preferably from 50 nCi to 150 mCi per dose, based on a 70 kg patient weight, is injected. Injection may be intravenous, intraarterial, intralymphatic, intrathecal, or intracavitary, and may be repeated more than once. It may be advantageous for some therapies to administer multiple, divided doses of radiolabeled polypeptides or polypeptide mixtures, e.g., in the range of 20-120 mCi (70 kg patient), thus providing higher cell-killing doses to the neoplasm without usually effecting a proportional increase in radiation of normal tissues Therapy using labeled polypeptides is advantageously used as a primary therapeutic treatment, but may also be used in combination with other anti-neoplastic therapies, e.g., radiation and chemotherapy, and as an adjunct to surgery. The administration of such conjugated polypeptides is particularly useful in the case where small metastases cannot be surgically removed.

Combination of a Polypeptide with Other Anti-Neoplastic Therapies

Chemotherapeutic agents and/or radiation and/or surgical removal of the neoplasm can optionally be combined with any of the methods of the present invention. Classes of compounds that can be used as the chemotherapeutic agent include: alkylating agents, antimetabolites, natural products and their derivatives, hormones and steroids (including synthetic analogs), and synthetics. Examples of alkylating agents (e.g., nitrogen mustards, ethylenimine derivatives, alkyl sulfonates, nitrosoureas and triazenes) include Uracil mustard, Chlormethine, Cyclophosphamide (Cytoxan®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide. Antimetabolites (including folic acid antagonists, pyrimidine analogs, purine analogs and adenosine deaminase inhibitors) may include, for example, Methotrexate, 5-Fluorouracil, Floxuridine, Cytarabine, 6-Mercaptopurine, 6-Thioguanine, Fludarabine phosphate, Pentostatine, and Gemcitabine. Natural products and their derivatives (including vinca alkaloids, antitumor antibiotics, enzymes, lymphokines and epipodophyllotoxins) may also be used and include, for example, Vinblastine, Vincristine, Vindesine, Bleomycin, Dactinomycin, Daunorubicin, Doxorubicin, Epirubicin, Idarubicin, paclitaxel (paclitaxel is commercially available as Taxol, Mithramycin, Deoxyco-formycin, Mitomycin-C, L-Asparaginase, Interferons (especially IFN-alpha), Etoposide, and Teniposide. Hormones and steroids (including synthetic analogs) include, for example, 17-alpha-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, or Zoladex. Exemplary synthetics (including inorganic complexes such as platinum coordination complexes) include Cisplatin, Carboplatin, Hydroxyurea, Amsacrine, Procarbazine, Mitotane, Mitoxantrone, Levamisole, and Hexamethylmelamine.

Methods and dosages for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the disclosure of which is incorporated herein by reference.

The following examples are provided for the purpose of illustrating the invention and should not be construed as limiting.

The Sequence Listing submitted herewith on compact disc is incorporated herein by reference.

Example 1

Materials and Methods

Cell Culture

Human lung squamous cell carcinoma cell line LOU-NH91 was cultured in RPM1-1640 media (PAA, Vienna, Austria) supplemented with 20% fetal calf serum (FCS), 2 mM glutamine and penicillin/streptomycin (both 1%) and incubated in a humidified, 5% $CO_2$ atmosphere at 37° C. For the assays described, cells were grown to sub-confluency, detached with trypsin/EDTA and washed twice with phosphate-buffered saline (PBS) before use.

Producing Hybridomas

We immortalized lymphocytes by fusing them to the HAB-1 heteromyeloma as follows.

We washed the HAB-1 heteromyeloma cells twice with RPMI 1640 (PAA, Vienna, Austria) without additives and centrifuged the cells for 5 minutes at 1500 rpm. We then thawed frozen lymphocytes obtained from either the spleen or the lymph nodes and we washed these cells twice with RPMI 1640 without additives and centrifuged these cells at 1500 rpm for 5 minutes. Both the HAB-1 and the lymphocyte cell pellets were resuspended in 10 ml RPMI 1640 without additives and were counted in a Neubauer cell counting chamber. We washed the cells again, added the HAB-1 cells and the lymphocytes together in a ratio of 1:2 to 1:3, mixed them, and centrifuged the mixture for 8 minutes at 1500 rpm. We pre-warmed Polyethylene Glycol 1500 (PEG) to 37° C. and carefully let the PEG run drop-wise onto the pellet while slightly rotating the 50 ml tube. Next, we gently resuspended the pellet and rotated the tube for exactly 90 seconds in a 37° C. water bath. We washed the cells twice with a full 10 ml pipette of RPMI without additives and centrifuged the cells for 5 minutes at 1500 rpm. We added 1 ml of RPMI 1640 with HAT supplement (PAA, Vienna, Austria) and 10% FCS, 1% glutamine, and 1% penicillin/streptomycin ("RPMI 1640 HAT") into each well of a 24-well plate. The cell pellet was dissolved in RPMI 1640 HAT and 0.5 ml of the cells was added to each well of the 24-well plate. We then placed the 24-well plates into a 37° C. incubator and changed the RPMI 1640 HAT medium weekly. After four to six weeks, the cell culture supernatants were screened for antibody production in an enzyme-linked immunosorbent assay (ELISA).

Using this protocol, approximately 80% to 90% of the triomas generated are viable and approximately 50% secrete immunoglobulins. Positive clones were tested immunohistochemically on autologous tumor tissue sections and clones that showed a positive reaction were subsequently re-cloned.

cDNA Synthesis and RT-PCR

To obtain the sequence of the antibody, we isolated whole RNA from the trioma using the RNASE Kit from Qiagen. Total RNA may also be prepared using methods standard in the art, e.g., those described in Krenn et al. (Clin. Exp. Immunol. 115:168-175, 1999). cDNA synthesis from total RNA obtained from hybridoma cell line LM-1 (DSMZ Accession No. DSM ACC2623) was performed with 5 µg total RNA using Gibco BRL (Eggenstein, Germany) M-MLV Reverse Transcriptase according to the manufacturer's instructions. The amplification of $V_H$ and $V_L$ genes was carried out in a 25 µl volume with 1.75 mM $MgCl_2$, 0.4 pM primer, 200 µM of each dNTP, and 1U Taq polymerase (MBI Fermentas, St. Leon-Rot, Germany). The PCR-products were amplified using the following cycle profiles: 95° C. for 2 min, followed by 35 cycles of 94° C. for 30 sec; 65° C. for 30 sec (for VH3 and VH4 primers), 60° C. for VH1, VH2, VH5, VH6 and 52° C. for VL primers respectively; a final extension at 72° C. for 4 min.

Sequencing the Antibody

The PCR products were purified using gel electrophoresis through 2% agarose (Roth, Karlsruhe, Germany) followed by gel extraction of the PCR product using a Jetsorb gel extraction kit (Genomed, Bad Oeynhausen, Germany). The PCR products were then cloned using the pCR-Script Amp SK+ cloning kit (Stratagene, Heidelberg, Germany). Ten positive clones were sequenced using the DyeDeoxy termination cycle sequencing kit (Applied BioSystems Inc., Weiterstadt, Germany) and analysed with an ABIPrism373 automated DNA sequencer (both strands were sequenced using T3 and T7 primers). The sequences were analysed using the DNASIS for Windows sequence comparison software and the GenBank and IMGT/V-QUEST databases. The International Immunogenetics ("IMGT") database is coordinated by Marie-Paule Lefranc at the Université Montpellier, Montpellier, France.

Immunohistochemical Staining of Paraffin Sections

Paraffin-embedded human tissues were sectioned (2 µm), the paraffin was removed as follows:

Two xylene washes for 5 minutes each,
Two 100% ethanol washes for 5 minutes each,
One methanol (70 ml) and $H_2O_2$ (500 µl) was for 5 minutes,
Two 90% ethanol washes for 3 minutes each,
Two 80% ethanol washes for 3 minutes each,
Two 70% ethanol washes for 3 minutes each, and
washed in Tris/NaCl (3 grams Tris, 40.5 grams NaCl in 5 liters of distilled $H_2O$ and pH adjusted to 7.4 with HCl).

The slides containing the tissue sections were incubated in 300 ml distilled $H_2O$ and cirtic acid (pH 5.5) in a pressure cooker at 100° C. for 5 minutes. The slides were blocked for 15 minutes with 150 µl of 0.5% Bovine Serum Albumin Fraction V ("BSA;" Roth, Karlsruhe, Germany) in phosphate buffered saline ("PBS") per slide, and washed once with Tris/NaCl.

The sections were incubated with the primary antibody (e.g., LM-1, unrelated, human monoclonal IgM antibodies (Chrompure IgM, Dianova, Hamburg, Germany, 10 µg/ml), CK8 antibody, or mouse CAM 5.2 antibody) diluted 1:50 (CAM 5.2 diluted 1:10) with BSA/PBS (Dako, Hamburg, Germany) for 2.5 hours in a humidified incubator at 37° C. The sections were then washed three times with Tris/NaCl (3 grams Tris, 40.5 grams NaCl in 5 liters of distilled $H_2O$ and pH adjusted to 7.4 with HCl), followed by incubation with the secondary antibody (e.g., peroxidase-labeled rabbit anti-human or rabbit anti-mouse conjugate (Dako)) diluted 1:50 in PBS containing 30% rabbit serum at room temperature ("RT") for 1 hour. After washing three times with Tris/NaCl the tissue sections were incubated in PBS for 10 minutes before staining with 150 µl diaminobenzidine (0.05%)-hydrogen peroxide (0.02%) for 10 minutes at RT. The reaction was stopped using running tap water (10-15 minutes) and the sections counterstained with hematoxylin. After mounting with glycerol-gelatin, the sections were analyzed using light microscopy.

Immunohistochemical Staining of Cryo-Sections from Autologous Tumors

Frozen human tissues were sectioned (4 µm) air-dried for two hours, fixed in acetone, air-dried for 30 minutes, and washed with Tris/NaCl (3 grams Tris, 40.5 grams NaCl in 5 liters of distilled H$_2$O and pH adjusted to 7.4 with HCl). The cryo-sections were then blocked with PBS containing 3% milk powder for 15-30 minutes at RT. After washing three times with Tris/NaCl the sections were incubated with LM-1 human IgM antibodies, unrelated human monoclonal IgM (Chrompure IgM, Dianova, 10 µg/ml), CK8 (diluted 1:50 with BSA/PBS; Dako) or mouse CAM 5.2 antibody (diluted 1:10 with BSA/PBS) for 30 minutes at RT. The sections were washed three times with Tris/NaCl, followed by incubation with secondary antibodies (peroxidase-labeled rabbit anti-human or rabbit anti-mouse conjugate 1:50 in 70% PBS and 30% human serum) for 30 minutes at RT. After washing three times with Tris/NaCl and incubation in PBS for 10 minutes, the sections were stained with diaminobenzidine (0.05%)-hydrogen peroxide (0.02%) for 10 minutes at RT. The reaction was stopped under running tap water and the sections counterstained with hematoxylin. After mounting with glycerol-gelatin, the sections were analyzed using light microscopy.

Preparation of Tumor Cell Membrane Extracts

Isolation of membrane proteins from tumor cells was performed as described using standard methods in the art, as described, for example, in Hensel et al. (Int. J. Cancer 81:229-235, 1999). In particular, confluent tumor cells (e.g., LOU-NH91 cells) were washed twice with PBS, harvested with a cell scraper, centrifuged, and resuspended in hypotonic buffer (20 mM HEPES, 3 mM KCl, 3 mM MgCl$_2$) and incubated for 15 minutes on ice. The cells were then sonicated for 5 minutes and the nuclei were pelleted by centrifugation at 10,000×g for 10 min. The supernatant was centrifuged for 40 minutes at 100,000×g in a swing-out rotor to pellet the membranes. After washing the pellet with hypotonic buffer, the pellet was resuspended in membrane lysis buffer (50 mM HEPES pH 7.4, 0.1 mM EDTA, 10% glycerol, and 1% Triton X-100). Complete protease inhibitor (Boehringer, Mannheim, Germany) also was added to all solutions.

Western Blotting

Western blots were preformed using standard techniques as described, for example, in Hensel et al. (Int. J. Cancer 81:229-235, 1999). In short, blotted nitrocellulose membranes were blocked with PBS containing 3% low fat milk powder, followed by incubation for 1 hour with 20-40 µg of LM-1 human IgM antibodies or unrelated human control IgM (ChromPure IgM, Dianova). The secondary antibody (peroxidase-coupled rabbit anti-human IgM antibody 1:1,000, Dianova) was detected with the SUPERSIGNAL chemiluminescence kit from Pierce (KMF, St. Augustin, Germany).

Cytospin Preparation

The adherent growing cells were detached by adding Trypsin/EDTA (PAA, Vienna, Austria) followed by a 5 minute incubation in an humidified incubator (37° C., 5% CO$_2$) and centrifugation for 5 minutes at 1,500 rpm. The cells then were washed twice with 10 ml of RPMI-1640 cell culture medium (PAA, Vienna, Austria). The cell number was adjusted to a density of 1×10$^5$ cells/ml. From this solution, 100 µl were centrifuged onto microscope slides with a cytospin centrifuge (CYTOSPIN 2, Shandon, UK) for 2 minutes at 50 rpm. The resultant cytospins were dried for at least 2 hours and stained as specified below.

Immunoperoxidase Staining of Cytospins and Cryosections

Cytospins were dried for at least two hours at room temperature or cryosections were dried for at least two hours after they were cut. The sections or cytospins were then fixed for 10 minutes in acetone. The fixed cryosections/cytospins were dried for 30 minutes at room temperature, washed three times with Tris-NaCl (3 grams Tris, 40.5 grams NaCl in 5 liters of distilled H$_2$O and pH adjusted to 7.4 with HCl), and placed into Tris/NaCl for 5 minutes. The cryosections/cytospins were blocked for 15-30 minutes with 3% milk powder in PBS (100 µl per cryosection/cytospin) and washed three times with Tris-NaCl. The cryosections/cytospins were incubated in 100 µl of primary antibody per cryosection/cytospin (e.g., at 20 µg/ml in 0.5% BSA/PBS; CK 8 at 1:50 in BSA/PBS; CAM 5.2 at 1:10 in BSA/PBS; or RPMI 1640 media (PAA, Vienna, Austria) as a negative control) for 30 minutes in a humidified chamber at room temperature. Following the incubation, the cryosections/cytospins were washed three times with Tris-NaCl.

The cryosections/cytospins were then incubated in 100 µl of a solution containing the secondary antibody (70% PBS+ 30% rabbit or human serum+e.g., 1:50 rabbit anti-mouse antibody, peroxidase coupled or 1:50 rabbit anti-human IgM antibody, peroxidase coupled; Dako, Hamburg, Germany) per cryosection/cytospin for 30 minutes in a humidified chamber at room temperature and washed three times with Tris-NaCl and placed into PBS for 10 minutes. The cryosections/cytospins where then incubated for 10 minutes in 100 µl of a solution containing 0.05% diaminobenzidine and 0.02% hydrogen peroxide (Sigma, Taufkirchen. (München), Germany). Following the incubation, the cryosections/cytospins were washed with distilled H$_2$O and placed into a hematoxylin staining solution (Roth, Karlsruhe, Germany) for 5 minutes. The cryosections/cytospins were then rinsed for 15 minutes under running tap water, washed with distilled H$_2$O, and cover with pre-warmed glycerol-gelatin.

The following experiments were carried out using the above materials and methods.

Example 2

Generation of the Cell Line Expressing the LM-1 Monoclonal Antibody

As described above, we obtained the LM-1 monoclonal antibody expressing hybridoma by fusing lymphocytes obtained from the lymph nodes of a cancer patient with the heteromyeloma cell line HAB-1 (Faller, et al., Br. J. Cancer 62:595-598, 1990). The lymphoid sources were not pre-selected in terms of the age or sex of the patient. The resultant cell is a type of hybridoma known as a trioma, as it is the fusion of three cells. Like normal B-lymphocytes, this trioma has to ability to produce antibodies. The specificity of the antibody is determined by the specificity of the original lymphocyte from the patient that was used to generate the trioma.

The hybridoma supernatants were screened for antibody production using an ELISA assay. Following ELISA, antibodies were primarily tested immunohistochemically against their autologous tumor for tumor specific reactivity. The LM-1 antibody was generated from the lymphocytes of a patient with lung adenocarcinoma.

The amino acid sequence (SEQ ID NO:2) and the nucleic acid sequence (SEQ ID NO:1) of the variable region of the heavy chain of human monoclonal antibody LM-1 are shown in FIG. 7. As indicated in FIG. 7, CDR1 of the LM-1 variable region heavy chain spans nucleotides 44-66 which encode amino acids 16-22, CDR2 spans nucleotides 109-156 which encode amino acids 37-52, and CDR3 spans nucleotides 253-

309 which encode amino acids 85-103. In addition, the D region spans nucleotides 265-293 and the J region spans nucleotides 294-312.

Example 3

Immunohistochemical Characterization of an Antibody

To characterize the monoclonal antibody secreted by a hybridoma, we tested the antibody against a panel of normal and tumor tissues using an immunoperoxidase assay as described in the materials and methods. This assay provided us with an overview of which tissues were stained by the antibody and of the distribution of the antigen.

Antibodies that are specific for tumor cells and not for normal tissue were further characterized. First, we tested these antibodies against the same types of tumors from different patients. We then tested these antibodies against tumors of other organs and, finally, against normal tissues. Using these assays, we identified the human LM-1 monoclonal antibody. This tumor reactive antibody is of the IgM/λ isotype (see Table 1).

TABLE 1

Origin of the LM-1 Monoclonal IgM Antibody and Clinical Data of Cancer Patients

| Antibody | Organ | Tumour type | Tumour stage | Tumour grade | Age | Sex | Source of Lymphocytes | Ig Class |
|---|---|---|---|---|---|---|---|---|
| LM-1 | Lung | Adenocarcinoma | T2N1 | G3 | 45 | M | Lymph Node | IgM/λ |

To investigate the genetic origin of this human monoclonal IgM antibodies the $V_H$ gene was amplified, cloned and sequenced. The sequence was compared with germ-line sequences in the IMGT/V-QUEST database to identify the most homologous germ-line genes and to detect somatic mutations. The results are represented in Table 2. The degree of identity of the nucleotide sequences of the $V_H$ segment to those of the closest reported germ-line $V_H$ genes was approximately 99.6% as summarized in Table 2.

TABLE 2

Characterization of Variable Heavy Region of Monoclonal IgM Antibody LM-1

| | Heavy chain | | | |
|---|---|---|---|---|
| Antibody | Germ-line gene | Homology (%) | R/S Frame | R/S CDR |
| LM-1 | IGHV 4-30.01/ 4-31*01 | 99.6 | 1/0 | 0/0 |

Genes of the VH4 gene family expressed the LM-1 antibody. The high homology of the VH regions to the germ-line genes and the low R/S ratio, which is an indicator for affinity maturation of antibodies, indicates that none of the antibodies underwent affinity maturation by somatic mutation due to antigen contact. The data indicate that the LM-1 antibody belongs to the family of naturally occurring, non-affinity matured antibodies.

After initial testing on autologous tumors, the reaction patterns of the antibodies were investigated in greater detail using immunohistochemical staining on a variety of paraffin- and cryo-embedded carcinomas and normal tissues. The LM-1 antibody exhibited no binding activity with normal tissues (Table 3).

TABLE 3

Reaction Pattern of the Monoclonal IgM Antibody LM-1 on Normal Tissues

| Tissue | LM-1 | CAM 5.2 | M6 (IgM-Control) |
|---|---|---|---|
| Stomach | − | + | − |
| Colon | − | + | − |
| Lung | − | − | − |
| Esophagus | − | − | − |
| Urinary bladder | − | − | − |
| Prostate | − | − | − |
| Breast | − | − | − |
| Pancreas | − | − | − |
| Small Intestine | − | + | − |

In contrast, the LM-1 antibody stains a variety of different tumor tissues (for details see Table 4).

TABLE 4

Reaction Pattern of the Monoclonal IgM Antibody LM-1 on Tumor Tissues

| Tissue | Carcinoma type | LM-1 +/− | CAM5.2 | M6 (IgM-Control) |
|---|---|---|---|---|
| Stomach | Adeno/diffuse | 5/0 | + | − |
| | Adeno/intestinal | 2/1 | + | − |
| Colon | Adeno | 3/0 | + | − |
| Lung | Adeno | 5/1 | + | − |
| | Squamous cell | 6/0 | +(CK5/6) | − |
| Esophagus | Squamous cell | 3/0 | +(CK5/6) | − |
| | Adeno (Barrett) | 4/0 | + | − |
| Pancreas | Adeno | 6/0 | + | − |
| Urinary bladder | Urothel | 1/0 | + | − |
| Kidney | Renal cell | 1/0 | − | − |
| Prostate | Adeno | 7/0 | + | − |
| Breast | Invasive (ductal) | 4/0 | + | − |
| | Invasive (lobular) | 4/0 | + | − |
| Ovary | Adeno | 3/0 | + | − |
| Uterus | Adeno | 3/0 | + | − |

Antibody LM-1 gave a broad staining pattern on a variety of tumor tissues that were tested (FIG. 1). The positive control antibodies used in these experiments were a mouse monoclonal antibody against human cytokeratin 5/6 ("CK 5/6;" Dako A/S, Denmark) for squamous cell carcinoma of the lung and esophagus and a mouse monoclonal antibody against human cytokeratin ("CAM 5.2;" Becton Dickinson, New Jersey). Additional positive control antibodies (AE1/AE3 for adenocarcinoma of the colon and antibody CK8 for invasive ductal carcinoma of the breast) were used in the experiments shown in FIG. 1.

Figure 6:
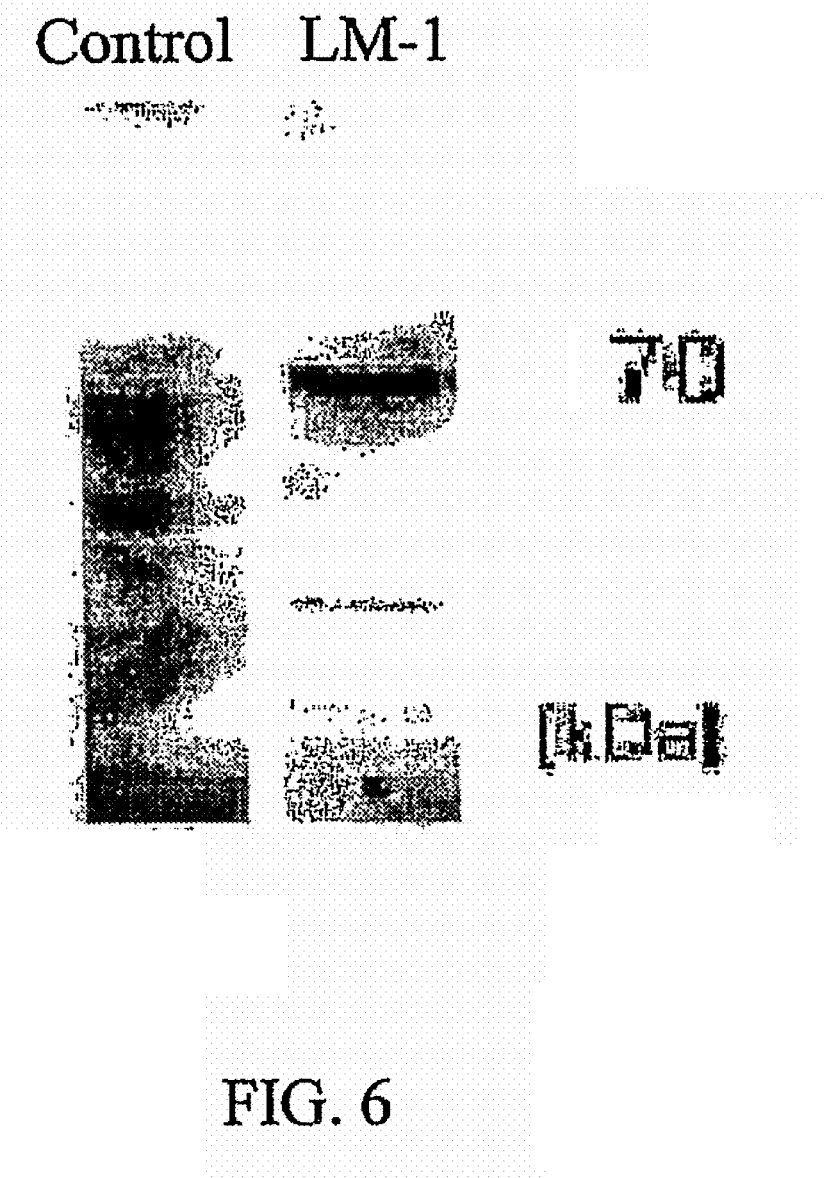
FIG. 6 is a Western blot showing the proteins recognized by human monoclonal antibody LM-1 on membrane extracts of lung carcinoma cell line LOU-NH91. Antibody LM-1 recognizes one main band with a molecular weight of approximately 70 kDa. As a control in these experiments, unrelated human IgM was added at a similar concentration to rule out non-specific binding.

To examine the antigen recognized by the LM-1 antibody, Western blots were performed with membrane extracts of established lung carcinoma cell line LOU-NH91. Antibody LM-1 reacted with an antigen with an approximate molecular weight of 70 kDa (FIG. 6). To rule out non-specific binding of IgM antibodies to membrane extracts, unrelated human control IgM was used as control.

Moreover, the LM-1 monoclonal antibody also specifically stains a number of carcinoma cell lines. In particular, the LM-1 antibody specifically binds lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), and lung squamous cell carcinoma cell line LOU-NH91 (DSMZ accession number ACC 393). Slides of these cells were stained according to the cytospin protocol described in the materials and methods section.

Example 4

Determining Whether an Antibody Inhibits Cell Proliferation

Cell proliferation may be assayed by a number of methods that are standard in the art, for example, by the reduction of tetrazolium salts. The yellow tetrazolium salt 3-(4,5-dimethylthiazol-2-yl)-2,5-diphenyltetrazolium bromide ("MTT") (Sigma, St. Louis, Mo.), is reduced by metabolically active cells, in part by the action of mitochondrial dehydrogenase enzymes to generate reducing equivalents such as NADH and NADPH. The resulting intracellular purple formazan can be solubilized and quantified by spectrophotometric means. The MTT cell proliferation assay measures the rate of cell proliferation and, when metabolic events lead to apoptosis, the reduction in cell viability.

For the MTT assay, we trypsinized cells (EPLC-272H or LOU-NH91) and resuspended the cells in 10 ml of RPMI-1460 medium containing 10% Fetal Calf Serum ("FCS") (20% FCS for LOU-NH91), 1% glutamine, and 1% penicillin/streptomycin (complete medium). The cells were then counted and diluted to $1 \times 10^6$ cells/ml. 50 µl of this suspension were pipetted into wells of a 96-well plate, resulting in approximately $5 \times 10^4$ cells/well. The first row of wells was left empty. We then added 50 µl of the antibody diluted in complete medium to each well. The 96-well plate was then incubated for 24 or 48 hours in a 37° C. incubator. After the incubation period, 50 µl MTT solution (5 mg/ml in PBS) were added to each well. The 96-well plate was incubated for 30 minutes at 37° C. and centrifuged for 5 minutes at 800×g. The supernatant was aspirated, 150 µl of dimethylsulphoxide (DMSO) were added to each well, and the cell pellet was resuspended. Absorption was determined at a wavelength of 540 nm and at a reference wavelength of 690 nm in an ELISA reader.

Figure 2:
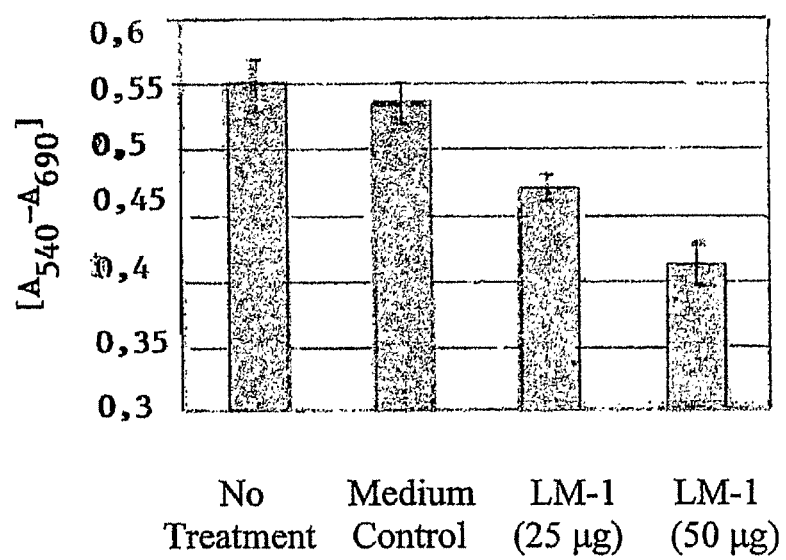
FIG. 2 is a graph depicting the functional analysis of antibody LM-1 in vitro. The consequences of antibody treatment on the proliferation of different carcinoma cell lines were measured using a 3-(4,5-dimethylthiazol-2-yl)-2,5-diphenyltetrazolium bromide ("MTT") proliferation assay.

As shown in FIG. 2, after 24, monoclonal antibody LM-1 inhibited cell proliferation of lung carcinoma cell line LOU-NH91. In these experiments, LOU-NH91 cells were incubated with the LM-1 monoclonal antibody, with depleted supernatant, or without an antibody for 24 hours. The y-axis shows the difference in absorbance at 540 nm and 690 nm ($A_{540}$-$A_{690}$). As is evident from these graphs, incubation with the LM-1 monoclonal antibody resulted in a decrease in cell proliferation and cell viability after both a 24 hour and a 48 hour incubation period.

Figure 3A:
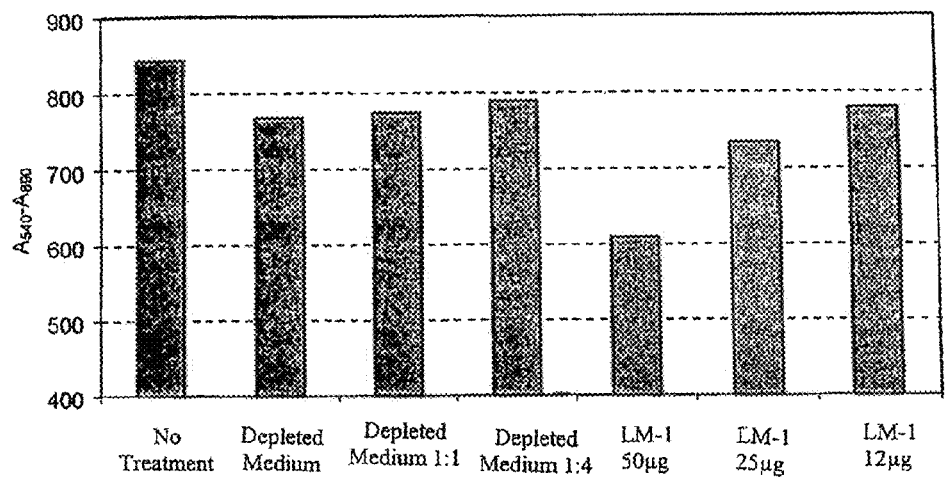
FIGS. 3A and 3B are a series of graphs of the results of MTT reduction assays for mitochondrial dehydrogenase activity showing that the LM-1 monoclonal antibody inhibits cell proliferation and decreases survival, or induces apoptosis of EPLC-272H epidermoid cell carcinoma of the lung cells after 24 hours of incubation (FIG. 3A) and after 48 hours of incubation (FIG. 3B).
Figure 3B:
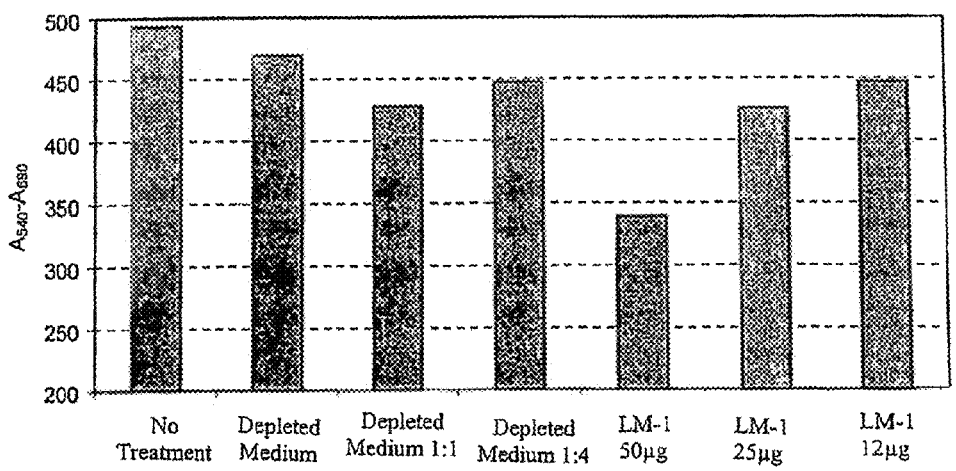

Further exemplary results of such experiments are depicted in FIGS. 3A and 3B. After 24 or 48 hours, monoclonal antibody LM-1 inhibited cell proliferation of human epidermoid cell carcinoma cell line EPLC-272H in a concentration-dependent manner, while the controls with depleted cell culture supernatant remained unchanged (FIGS. 3A and 3B).

Example 5

Determining Whether an Antibody Induces Apoptosis

A number of assays standard in the art may be used to determine if an antibody induces apoptosis of a cell.

For example, we used the CELL DEATH DETECTION ELISA$^{PLUS}$ (Roche, Mannheim, Germany) to analyze the extent to which the LM-1 antibody induce apoptosis. The cell death detection ELISA is based on a quantitative sandwich-enzyme-immunoassay principle using mouse monoclonal antibodies directed against DNA and histones, respectively. This assay allows the specific determination of mono- and oligo-nucleosomes which are released into the cytoplasm of cells which die from apoptosis.

Figure 4:
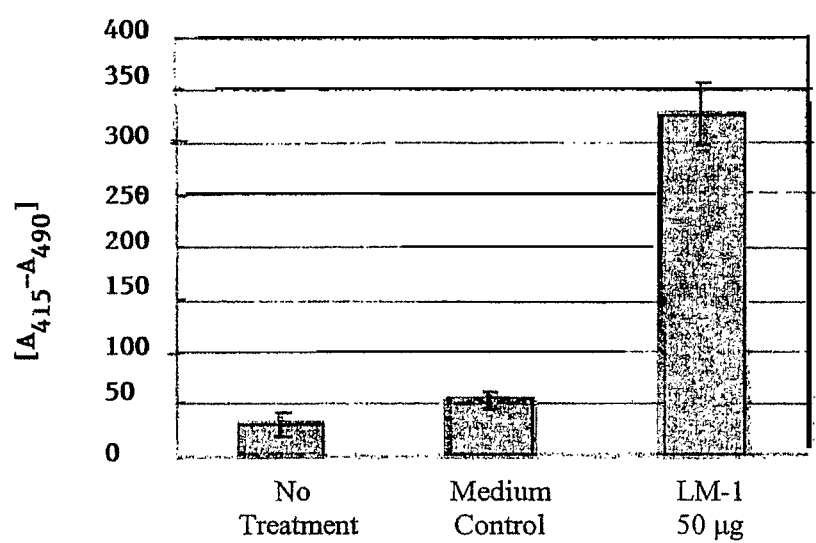
FIG. 4 is a graph showing that the LM-1 antibody induces apoptosis. In these experiments, apoptosis was detected using the Cell Death Detection ELISA$^{PLUS}$ apoptosis assay.
Figure 5A:
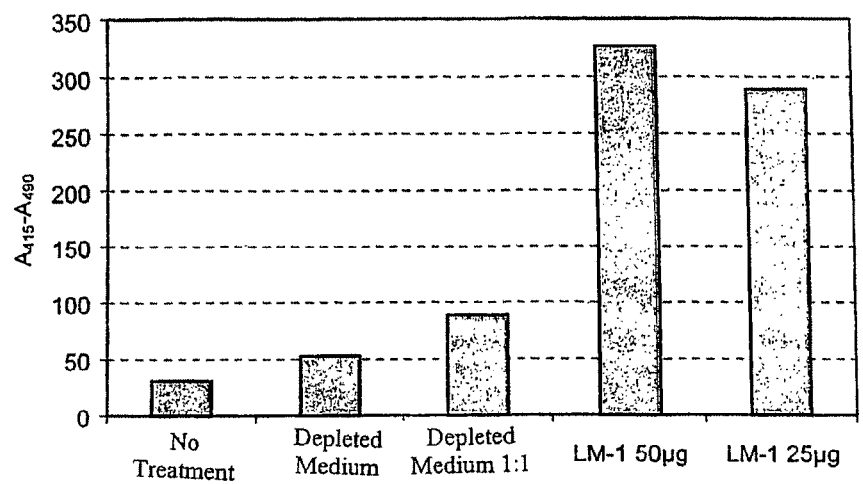
FIGS. 5A and 5B are a series of graphs of the results of a cell death ELISA showing that the LM-1 monoclonal antibody induces apoptosis of LOU-NH91 cells after 24 hours of incubation (FIG. 5A) and after 48 hours of incubation (FIG. 5B).
Figure 5B:
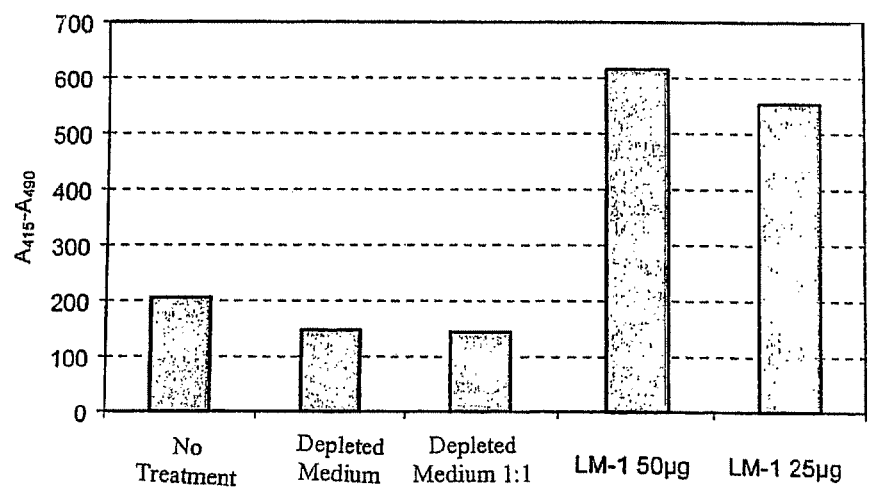

In particular, $1 \times 10^4$ tumor cells (LOU-NH91) were plated on 96-well plates and incubated in presence of different concentrations of the human IgM-antibody LM-1 for 24 hours at 37° C. and 7% $CO_2$ in an $CO_2$ incubator. Depleted cell culture supernatant with unrelated IgM antibodies served as negative control. After the incubation period, the cells were centrifuged for 10 minutes at 200×g and the supernatants were removed. The resulting cell pellets were then incubated with 200 µl lysis-buffer for 30 minutes at room temperature. After centrifugation 20 µl the supernatants were transferred into a streptavidin-coated microtiter plate (MTP) and 80 µl immunoreagent (a mixture of 10% Anti-Histone-Biotin, 10% Anti-DNA-peroxidase (Anti-DNA POD) and 80% incubation buffer) added before incubation for 2 hours at room temperature on a MTP shaker at 250 rpm. Following the incubation period, unbound components were removed by a washing step with incubation buffer. POD was determined photometrically with ABTS™ as a substrate (1 ABTS™ (2,2'-Azino-di[3-ethyl-bent-thiazolin-sulfonate]) tablet in 5 ml substrate buffer). Antibody-induced apoptosis was measured by determining the color intensity of the green precipitate that it formed as a result of this reaction using an ELISA reader at a wavelength of 415 nm in comparison to ABTS™ solution as a blank (reference wavelength of approximately 490 nm). Based on this color intensity, we calculated the level of the antibody-induced apoptosis. These experiments clearly showed that antibody LM-1 induces apoptosis in LOU-NH91 carcinoma cells after 24 hours of incubation (FIGS. 4 and 5A) and after 48 hours of incubation (FIG. 5B). The Y-axis in these figures is the difference between the absorbance at 415 nm and at the 490 nm reference wavelength ($A_{415}$-$A_{490}$) and the medium control is RPMI 1460 medium. The concentration of the LM-1 antibody was either 25 µg or 50 µg/ml in supernatant.

Example 6

In Vivo Imaging of a Neoplasm

A patient suspected of having a neoplasm, such as a lung carcinoma, may be given a dose of radioiodinated LM-1 antibody, or another tumor-specific polypeptide, and radiolabeled unspecific antibody using the methods described herein. Localization of the tumor for imaging may be effected according to the procedure of Goldenberg et al. (N. Engl. J. Med., 298:1384, 1978). By I.V. an infusion of equal volumes of solutions of $^{131}$I-LM-1 antibody and Tc-99m-labeled unspecific antibody may be administered to a patient. Prior to administration of the reagents I.V., the patient is typically pre-tested for hypersensitivity to the antibody preparation (unlabeled) or to antibody of the same species as the antibody preparation. To block thyroid uptake of $^{131}$I, Lugol's solution is administered orally, beginning one or more days before injection of the radioiodinated antibody, at a dose of 5 drops twice or three-times daily. Images of various body regions and views may be taken at 4, 8, and 24 hours after injection of the labeled preparations. If present, the neoplasm, e.g., a colorectal carcinoma, is detected by gamma camera imaging with subtraction of the Tc-99m counts from those of $^{131}$I, as described for $^{131}$I-labeled anti-CEA antibody and Tc-99m-labeled human serum albumin by DeLand et al. (Cancer Res. 40:3046, 1980). At 8 hours after injection, imaging is usually clear and improves with time up to the 24 hour scans.

Example 7

Treatment of a Neoplasm Using Labeled Antibody Mixtures

A patient diagnosed with a neoplasm, for example, a lung carcinoma, may be treated with the polypeptides of the invention as follows. Lugol's solution may be administered, e.g., 7 drops 3 times daily, to the patient. Subsequently, a therapeutic dose of $^{131}$I-LM-1 antibody may be administered to the patient. For example, a $^{131}$I dose of 50 mCi may be given weekly for 3 weeks, and then repeated at intervals adjusted on an individual basis, e.g., every three months, until hematological toxicity interrupts the therapy. The exact treatment regimen is generally determined by the attending physician or person supervising the treatment. The radioiodinated antibodies may be administered as slow I.V. infusions in 50 ml of sterile physiological saline. After the third injection dose, a reduction in the size of the primary tumor and metastases may be noted, particularly after the second therapy cycle, or 10 weeks after onset of therapy.

Example 8

Treatment Using Conjugated Antibodies

A patient diagnosed with a neoplasm, for example, a patient with a lung carcinoma that has metastasized to the chest, may be treated with solutions of $^{131}$I-LM-1, $^{10}$B-LM-1, and a Tc-99m labeled unspecific antibody. An amount of $^{131}$I-labeled LM-1 antibody (in 50 ml of sterile physiological saline) sufficient to provide 100 mCi of $^{131}$I activity based on a 70 kg patient weight may be administered to the patient. This dosage is equal to 3.3 mg of an antibody having 40-80 Boron atoms and 8-16 Boron-10 atoms per antibody molecule. The neoplasm is first precisely localized using the procedure of Example 6. In addition, Lugol's solution should be continuously administered to the patient, as in the previous example. A well-collimated beam of thermal neutrons may then be focused on the defined tumor locations. Irradiation with an external neutron beam dose of 400-800 rads, delivered in a period of from 8-20 min, is effected for each tumor locus, and is optionally repeated with administration of the tumor-locating antibody, with or without the radiolabel, at intervals adjusted on an individual basis, but usually not exceeding a total dose of 3200 rads unless simultaneous external irradiation therapy is indicated. If desired, in addition to this therapy, an anti-tumor agent, such as a chemotherapeutic agent, may also be administered to the patient.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

German Patent Application No. 103 11 248.0, U.S. Pat. Nos. 5,367,060 and 5,641,869, and International Patent Publication Nos. WO 03/076472 and WO 2004/005351, and all other references cited herein are hereby incorporated by reference.

We claim:

1. A purified antibody or binding fragment thereof comprising (i) a heavy chain variable region sequence, wherein the heavy chain variable region sequence comprises the full-length sequence of SEQ ID NO:2, and (ii) a light chain variable region sequence comprising the three CDRs of the light chain variable region of the deposited hybridoma DSM ACC 2623.

2. The purified antibody or binding fragment of claim 1, wherein the antibody or binding fragment specifically binds to one or more of lung adenocarcinoma cell line Colo-699 (DSMZ accession number ACC 196), lung adenocarcinoma cell line DV-90 (DSMZ accession number ACC 307), epidermoid lung carcinoma cell line EPLC-272H (DSMZ accession number ACC 383) or lung squamous cell carcinoma cell line LOU-NH91 (DSMZ accession number ACC 393).

3. The purified antibody or binding fragment of claim 1, wherein the antibody or binding fragment specifically binds to one or more of a diffuse-type stomach adenocarcinoma, an intestinal-type stomach adenocarcinoma, an adenocarcinoma of the colon, an adenocarcinoma of the lung, a squamous cell carcinoma of the lung, a squamous cell carcinoma of the esophagus, an adenocarcinoma of the pancreas, a urothel carcinoma of the urinary bladder, a renal cell carcinoma of the kidney, an adenocarcinoma of the prostate, an invasive ductal carcinoma of the breast, an invasive lobular carcinoma of the breast, an adenocarcinoma of the ovary, or an adenocarcinoma of the uterus.

4. The antibody of claim 1, wherein said antibody is a monoclonal antibody.

5. A method of treating lung cancer in a human, comprising administering the antibody or binding fragment of claim 1 to the human to reduce cancer cell proliferation.

6. The method of claim 5, wherein said lung cancer is a squamous cell carcinoma.

7. The method of claim 5, wherein said antibody is a monoclonal antibody.

* * * * *

SEQUENCE LISTING

```
<160> NUMBER OF SEQ ID NOS: 2

<210> SEQ ID NO 1
<211> LENGTH: 333
<212> TYPE: DNA
<213> ORGANISM: Homo sapiens

<400> SEQUENCE: 1
ccgaccctgt ccctcacctg cgctgtctct ggtggctcca tcagcagtgg tggttactac      60
tggagctgga tccgccagca cccagggaag ggcctggagt ggattgggta catctattac     120
agtgggagca cctactacaa cccgtccctc aagagtcgag ttaccatatc agtagacacg     180
tctaagaacc agttctccct gaagctgagc tctgtgactg ccgcggacac ggccgtgtat     240
tactgtgcga gagttgatgc gcgatatgat tacgtttggg ggagttatcg ttatgatgct     300
tttgatatct ggggccaagg aaccatggtc acc                                 333

<210> SEQ ID NO 2
<211> LENGTH: 111
<212> TYPE: PRT
<213> ORGANISM: Homo sapiens
```

```
<400> SEQUENCE: 2

Pro Thr Leu Ser Leu Thr Cys Ala Val Ser Gly Gly Ser Ile Ser Ser
1               5                   10                  15

Gly Gly Tyr Tyr Trp Ser Trp Ile Arg Gln His Pro Gly Lys Gly Leu
            20                  25              30

Glu Trp Ile Gly Tyr Ile Tyr Tyr Ser Gly Ser Thr Tyr Tyr Asn Pro
            35              40                  45

Ser Leu Lys Ser Arg Val Thr Ile Ser Val Asp Thr Ser Lys Asn Gln
        50              55              60

Phe Ser Leu Lys Leu Ser Ser Val Thr Ala Ala Asp Thr Ala Val Tyr
65                  70                  75                  80

Tyr Cys Ala Arg Val Asp Ala Arg Tyr Asp Tyr Val Trp Gly Ser Tyr
                85                  90                  95

Arg Tyr Asp Ala Phe Asp Ile Trp Gly Gln Gly Thr Met Val Thr
                100                 105                 110
```